(12) United States Patent
Lee et al.

(10) Patent No.: US 12,268,502 B2
(45) Date of Patent: Apr. 8, 2025

(54) BLOOD SAMPLING DEVICE AND METHOD OF USING THE SAME

(71) Applicant: Probus Medical Technologies Inc., Bellevue, WA (US)

(72) Inventors: Kyonghoon Lee, Redmond, WA (US); Hyung Jin Park, Goyang-si (KR); Jihong Lee, Seoul (KR); Mincheol Kim, Irvine, CA (US)

(73) Assignee: Probus Medical Technologies Inc., Bellevue, WA (US)

( * ) Notice: Subject to any disclaimer, the term of this patent is extended or adjusted under 35 U.S.C. 154(b) by 0 days.

(21) Appl. No.: 18/111,410

(22) Filed: Feb. 17, 2023

(65) Prior Publication Data

US 2023/0200694 A1    Jun. 29, 2023

Related U.S. Application Data

(63) Continuation of application No. PCT/US2021/046559, filed on Aug. 18, 2021.

(60) Provisional application No. 63/067,224, filed on Aug. 18, 2020.

(51) Int. Cl.
*A61B 5/151* (2006.01)
*A61B 5/15* (2006.01)

(52) U.S. Cl.
CPC .... *A61B 5/15113* (2013.01); *A61B 5/150022* (2013.01); *A61B 5/150412* (2013.01)

(58) Field of Classification Search
CPC ............ A61B 5/15113; A61B 5/15107; A61B 5/150053; A61B 5/150083; A61B 5/150106; A61B 5/150137; A61B 5/15126; A61B 5/15128; A61B 5/150412; A61B 5/150022; A61B 5/15186; A61B 5/15188; A61B 5/1519; A61B 5/15192; A61B 5/15194; A61B 5/155

See application file for complete search history.

(56) References Cited

U.S. PATENT DOCUMENTS

| | | | |
|---|---|---|---|
| 4,517,978 A * | 5/1985 | Levin | A61B 5/15113 D24/112 |
| 6,419,661 B1 * | 7/2002 | Kuhr | A61B 5/15117 604/47 |
| 8,690,798 B2 | 4/2014 | Douglas et al. | |
| 2004/0059256 A1 | 3/2004 | Perez | |

(Continued)

FOREIGN PATENT DOCUMENTS

| | | |
|---|---|---|
| JP | 2007-301105 A | 11/2007 |
| WO | 2008/056598 A1 | 5/2008 |

OTHER PUBLICATIONS

International Search Report and Written Opinion dated Dec. 9, 2021 in International Application No. PCT/US21/46559.

(Continued)

*Primary Examiner* — Shaun L David
*Assistant Examiner* — Rachael L Geiger
(74) *Attorney, Agent, or Firm* — K&L Gates LLP

(57) ABSTRACT

The present disclosure provides a lancing device that includes a lancet for piercing a user's skin and a lancing device body to drive the lancet. An actuator included in the lancing device body can drive the lancet to perform a linear reciprocating motion multiple times upon a single activation. Accordingly, the lancet may pierce the user's skin multiple times upon a single activation.

19 Claims, 15 Drawing Sheets

(56) References Cited

U.S. PATENT DOCUMENTS

| | | | |
|---|---|---|---|
| 2004/0098008 A1* | 5/2004 | Taylor | A61B 5/150442 |
| | | | 606/181 |
| 2005/0070819 A1* | 3/2005 | Poux | A61B 5/150099 |
| | | | 600/576 |
| 2006/0247671 A1 | 11/2006 | LeVaughn | |
| 2010/0106058 A1 | 4/2010 | Douglas et al. | |
| 2010/0145377 A1* | 6/2010 | Lai | A61B 5/15186 |
| | | | 606/181 |
| 2011/0106126 A1* | 5/2011 | Love | A61B 5/145 |
| | | | 606/182 |
| 2012/0143235 A1 | 6/2012 | Kuhr et al. | |
| 2012/0165698 A1* | 6/2012 | Kuhr | A61B 5/14532 |
| | | | 600/583 |
| 2020/0060587 A1 | 2/2020 | Bremer et al. | |

OTHER PUBLICATIONS

Japanese Office Action dated Feb. 6, 2024 in Japanese Patent Application No. 2023-512439.

* cited by examiner

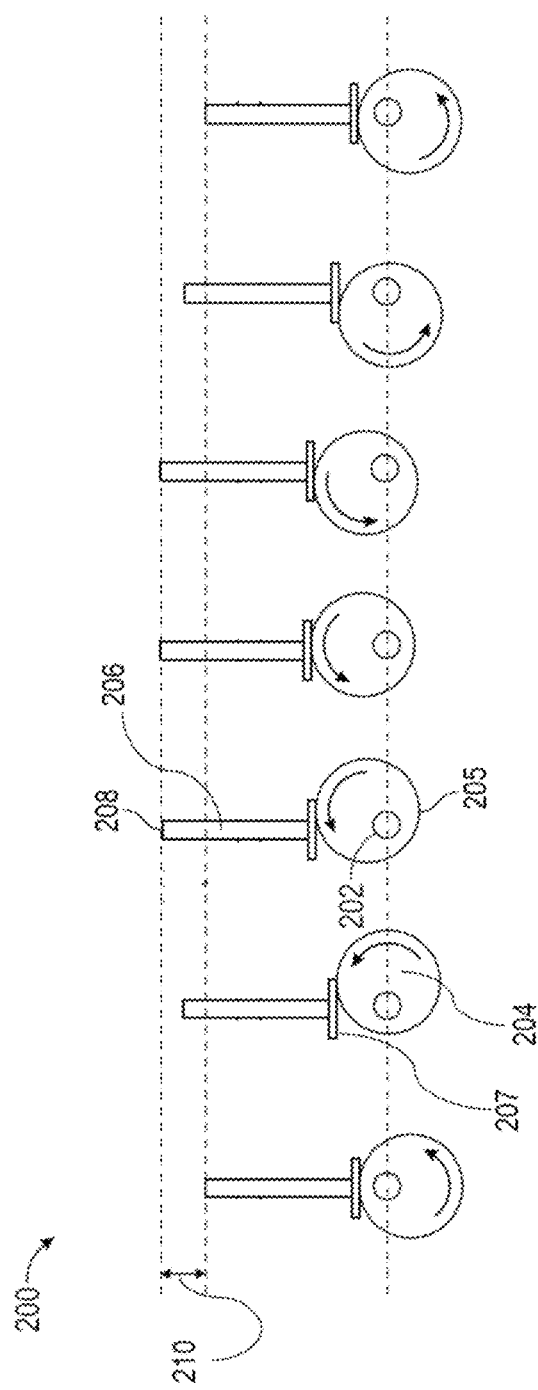

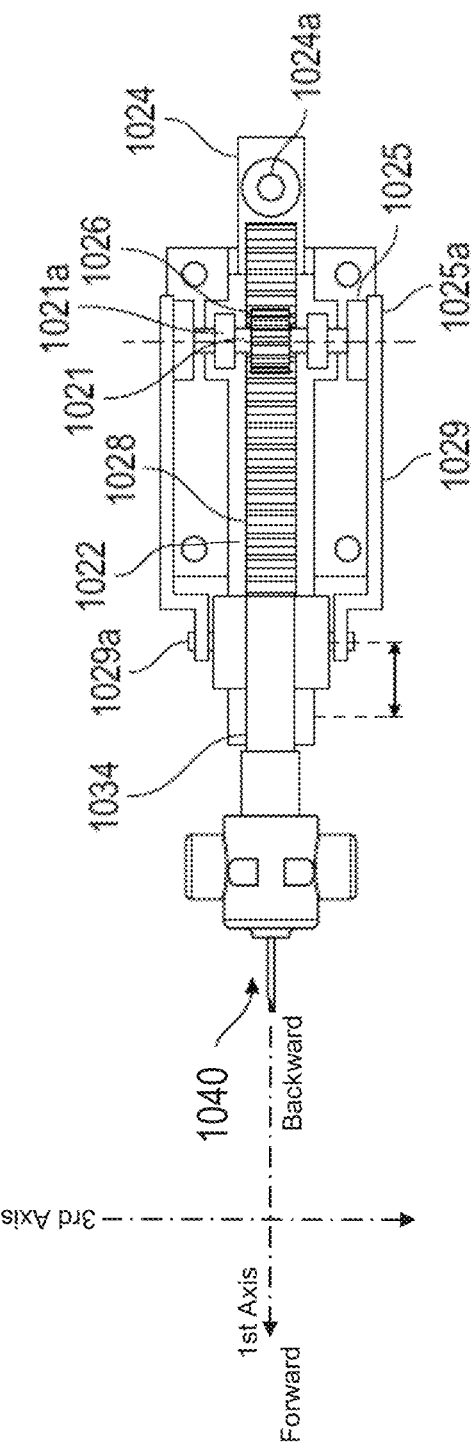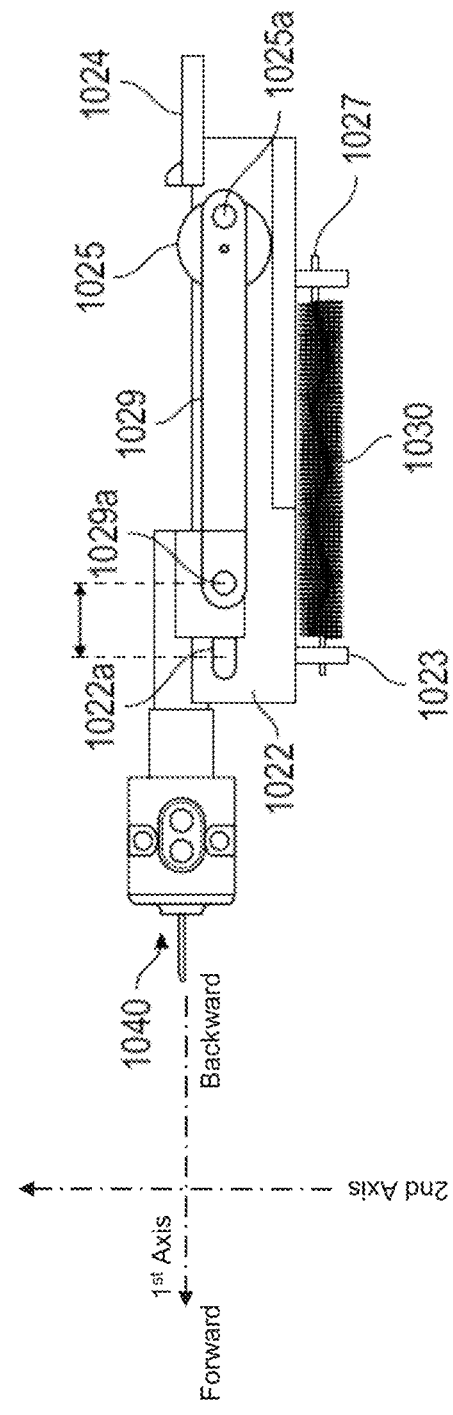

BLOOD SAMPLING DEVICE AND METHOD OF USING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to a lancing device for extracting a blood sample.

Discussion of Related Technology

A high level of interest exists in the healthcare community and industry for improving the technologies of sensing blood glucose levels. For blood glucose levels, blood samples need to be drawn from a person. A lancing device for collect blood samples comfortably without excessive pain is desired.

SUMMARY

One aspect of the present disclosure provides a lancing device which comprises: a lancet connector, a reciprocating actuator, a trigger, and a lancing device body. The lancet connector is for connecting with a lancet which comprises a lancet body and a needle fixed to and extending from the lancet body. The reciprocating actuator is operably connected to the lancet connector and configured to cause a linear reciprocating motion of the lancet connector along an axis. The trigger is configured to trigger the reciprocating actuator for causing the linear reciprocating motion of the lancet connector. The lancing device body comprises a main body portion, a lancet receiving portion and a tip portion that are arranged in order along the axis and integrated to form a single body.

In the foregoing lancing device, the main body portion is a hand-gripping portion configured for gripping with one hand of a person. The tip portion may comprise a skin contact surface or edge for contacting a skin area from which blood is to be sampled. The tip portion may further comprise an opening through which a needle is to travel. The lancet receiving portion connects the main body portion and the tip portion therebetween. The lancet connector may comprise an engagement portion configured to engage with a counterpart component of the lancet body for integrating the lancet with the lancet connector. Upon integrating the lancet with the lancet connector without triggering the reciprocating actuator, the lancet is generally located in or on the lancet receiving portion of the lancing device body, in which the needle extends in a forward direction along the axis away from the main body portion but does not extend beyond the skin contact surface in the forward direction such that a distal end of the needle would not and does not stab the skin area even if the tip portion is place on the skin area.

In response to triggering the reciprocating actuator with the trigger a single time, the reciprocating actuator is to cause the linear reciprocation motion of the lancet connector along the axis multiple times such that, when the lancet is integrated with the lancet connector, the lancet advances in the forward direction and retreats in a backward direction toward the main body portion along the axis, by which the distal end of the needle travels in the forward direction and in the backward direction multiple times through the opening between an advanced position and a withdrawn position. At the advanced position, the distal end of the needle is beyond the skin contact surface in the forward direction such that the needle could pierce the skin area if the skin area contacts the skin contact surface with the axis generally perpendicular to an imaginary plane of the skin area. At the withdrawn position, the distal end of the needle is closer to the main body portion along the axis than at the advanced position such that the needle could not pierce the skin area even if the skin area contacts the skin contact surface with the axis generally perpendicular to the imaginary plane of the skin area.

In the foregoing lancing devices, the reciprocating actuator may comprise a cam and a cam follower operably connected to the cam to generate the linear reciprocating motion in the forward direction and the backward direction along the axis. The lancet connector may be operably connected to cam follower for the linear reciprocating motion. The reciprocating actuator may further comprise a rack gear elongated generally in the axis and a pinion gear engaged with the rack gear. The pinion gear may be operably engaged with the rack gear and further operably connected to the cam such that sliding of the rack gear along the axis causes rotation of the pinion gear which further causes rotation of the cam about the cam axis. The reciprocating actuator may further comprise a handle disposed outside the main body portion and configured for pulling in the backward direction along the axis relative to the lancing device body. The handle may be connected to the rack gear for sliding the rack gear in the backward direction relative to the pinion gear when the handle is pulled in the backward direction.

In the foregoing lancing devices, the reciprocating actuator may comprise an electromechanical reciprocating actuator which may comprise a motor configured to generate a rotational force to rotate the cam. The trigger may comprise an electrical switch configured to turn on the motor. The reciprocating actuator may comprise a spring-loaded reciprocating actuator which may comprise a spring mechanism configured to store spring energy for generating a rotational force to rotate the cam, wherein the trigger may be configured to initiate a release of the spring energy. The trigger may be located on an exterior of the main body portion opposite to the tip portion such that, when the lancing device body may be gripped with one hand of the person, a finger of the same hand or another hand may apply an external force to the trigger, The reciprocating actuator may be configured to initiate an actuating operation in response to the external force applied to the trigger.

In the foregoing lancing devices, the reciprocating actuator may comprise a spring, a zigzag guide member, and an arm operably connected to the zigzag guide member. Here, the axis may be referred to as a first axis hereinafter, wherein the zigzag guide member may be configured to slide in the forward direction and in the backward direction along the first axis. The zigzag guide member may be operably connected to the spring such that, when the zigzag guide member moves in the backward direction, the spring may be to be compressed and store spring energy, and further such that, as the spring energy is released, the spring may be to extend and move the zigzag guide member in the forward direction, wherein the zigzag guide member may comprise a zigzag guide. The arm may comprise a first connection portion hingedly connected with the lancet connector for hinged rotation relative to the lancet connector about a second axis generally perpendicular to the first axis. The arm may comprise a second connection portion distanced from the first connection portion and engaged with the zigzag guide such that the second connection portion is to travel along the zigzag guide as the zigzag guide member moves in the forward direction and in the backward direction along the first axis. The arm may further comprise a third connection portion distanced from the first connection portion and engaged with a linear guide that is provided inside the main body portion and extends in a third axis generally perpendicular to the first axis and further to the second axis such that the third connection portion is to travel along the linear guide between two lateral positions in the third axis. The trigger may be configured to initiate a release of the spring energy. When the spring energy is released, the zigzag guide member slides in the forward direction, which causes the second connection portion to travel relative to the zigzag guide member along the zigzag guide, which further causes the hinged rotation of the arm about the second axis relative to the lancet connector, while the third connection portion of the arm travels along the linear guide between the two lateral positions in the third axis, which further causes the arm to push the lancet connector in the forward direction and pull the lancet connector in the backward direction to make the linear reciprocating motion of the lancet connector.

In the foregoing lancing devices, the zigzag guide may comprise at least one guide groove formed into the zigzag guide member that extends in a zigzag pattern when viewed in the second axis. The second connection portion of the arm may be sized and shaped for engaging with the at least one guide groove for traveling along the third axis as the zigzag guide member slides in the forward direction and in the backward direction. The zigzag guide may comprise at least one guide rail formed on the zigzag guide member that extends in a zigzag pattern when viewed in the second axis. The second connection portion of the arm may be sized and shaped for engaging with the at least one guide rail for traveling along the third axis as the zigzag guide member slides in the forward direction and in the backward direction. The linear guide may comprise a linear guide channel defined inside the main body and extending in the third axis. The third connection portion may be inserted in the linear guide channel and restricted to travel only along the linear guide channel between the two lateral positions in the third axis. The arm may be configured to hingedly rotate on an imaginary plane generally parallel to the plane defined by the first axis and the third axis. The second connection portion extends generally in the second axis further from the third connection portion to engage with the zigzag guide.

In the foregoing lancing devices, the reciprocating actuator may further comprise a spring guide configured to guide and keep the spring within a space it defines as the spring compresses and extends. The spring guide may comprise a spring contact surface which one end of the spring contacts. The zigzag guide member may be integrated with the spring guide, wherein, as the spring energy is released, the spring is configured to push the spring contact surface, which causes the spring guide to travel in the forward direction and accordingly moves the zigzag guide member in the forward direction relative to the main body portion. The reciprocating actuator may further comprise a handle connected to the spring guide and exposed outside the main body portion at an opposite end of the tip portion. The handle is configured to be pulled in the backward direction relative to the main body portion, which causes the spring guide to travel in the backward direction and compresses the spring. The reciprocating actuator may further comprise a latch configured to stop the movement of the handle in the backward direction beyond a predetermine point in the main body portion, at which the spring may be compressed and stores the spring energy, wherein the trigger may be configured to initiate the release of the spring energy.

In the foregoing lancing devices, the lancet receiving portion may comprise a channel extending in the axis for aligning the needle when connecting the lancet to the lancet connector. The lancet receiving portion may further comprise a recess configured to receive the lancet body and permits a linear movement of the lancet body along the axis when the lancet is connected to the lancet connector and the lancet advances in the forward direction and retreats in the backward direction along the axis. The lancet receiving portion may further comprise a step configured to block the lancet body from advancing further in the forward direction. The lancet may comprise at least one wing extending from the lancet body in a direction generally perpendicular to the extension of the needle from the lancet body.

Another aspect of the disclosure provides a lancing system comprising any of the foregoing lancing devices and a lancet comprising a lancet body and a needle extending from the lancet body. Still another aspect of the disclosure provides a method of sampling blood with any of the foregoing lancing device or system.

BRIEF DESCRIPTION OF THE DRAWINGS

FIGS. 5-7 illustrate example actuators to be used in the lancing device of FIG. 1.

FIG. 9 is a top view of the actuator according to the implementation of FIG. 8 in which the lancing device is in a relaxed or released state.

FIG. 10 is a side view of the actuator according to the implementation of FIG. 9.

DETAILED DESCRIPTION OF IMPLEMENTATIONS

Figure 1:
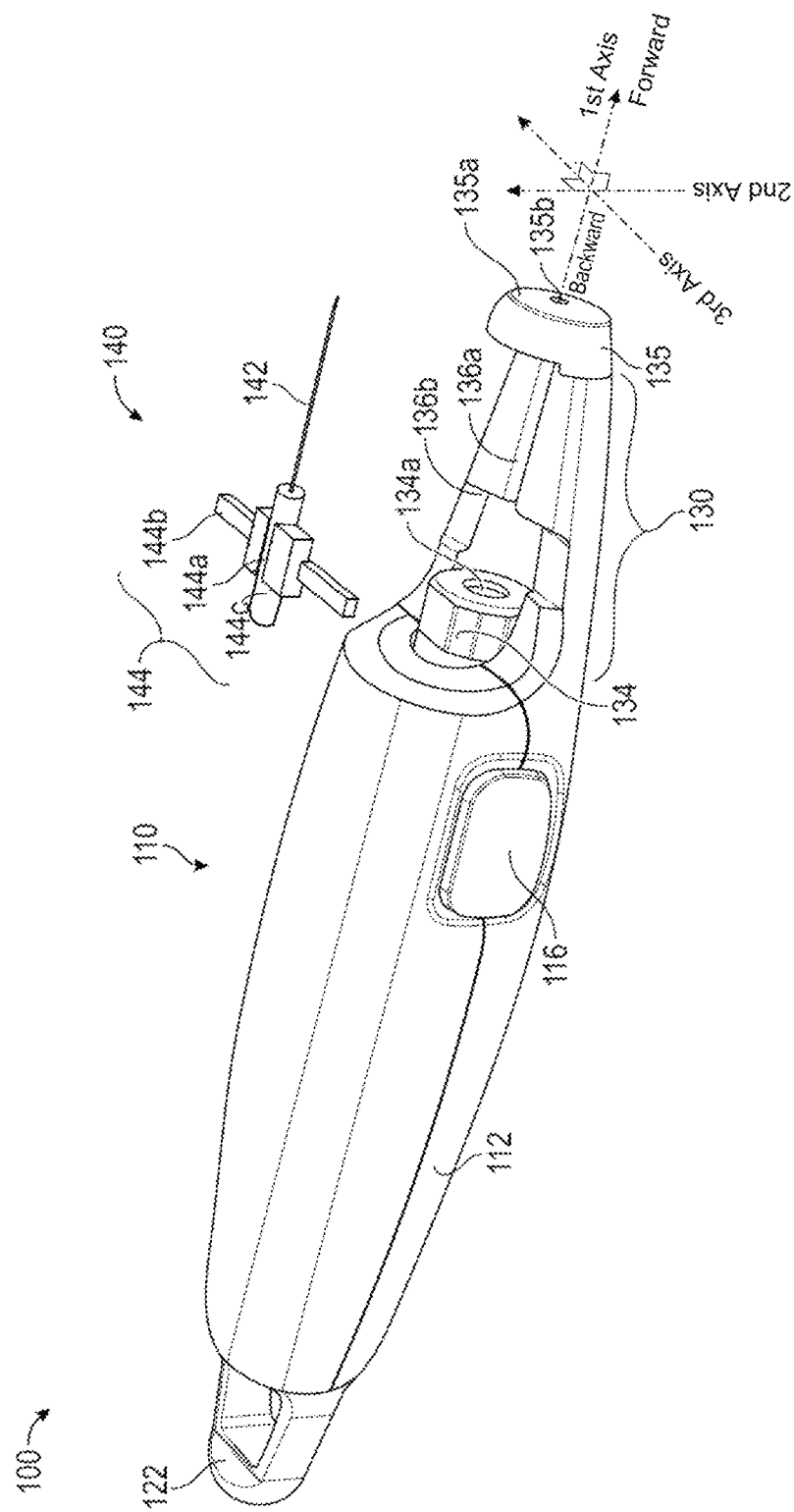
FIG. 1 is a perspective view of a lancing device and a lancet according to an implementation.

Hereinafter, implementations of the present invention will be described with reference to the drawings. These implementations are provided for better understanding of the present invention, and the present invention is not limited only to the implementations. Changes and modifications apparent from the implementations still fall in the scope of the present invention. Meanwhile, the original claims constitute part of the detailed description of this application.

Lancet and Lancing Device

A lancet includes a needle and is used to incise or penetrate skin to form an opening. A lancing device is used to operate the lancet and extract blood out of the skin. The lancet is coupled to the lancing device, which causes a linear reciprocating motion of the lancet toward and away from the skin of a selected location, such as finger or forearm. The tip of the lancet needle makes an opening by penetrating the skin, and pierces and ruptures capillaries underneath the skin. When blood flows out from the ruptured capillaries through the opening and gathers on the skin, the blood can be collected for a test, or a test instrument can be brought into contact with the blood for an immediate test.

Size of Needle and Pain

The gauge size or diameter of the needle can be determined to obtain the required amount of blood sample in a single operation. If the diameter of the lancet is too small, capillaries may not be ruptured enough and a sufficient amount of blood may not come out. Also, if the opening formed into the skin is too small, it will be difficult for the blood to flow out. However, if the diameter of the lancet needle is too large, the needle may hit or touch pain receptors distributed under the skin, which will cause pain every time the lancet is used. Some people are extremely sensitive to such pain. Diabetic patients who lance 3 to 4 times a day may find this procedure uncomfortable. In addition, calluses may develop when the lancet is used repeatedly in one spot.

Multiple Lancing

A lancet needle having a smaller diameter is less likely to touch pain receptors under skin and accordingly may reduce the discomfort and pain when collecting blood using the lancet. If a small diameter lancet needle is used to lance the same skin location multiple times, more capillaries could be ruptured and more blood could be obtained without causing the discomfort or pain from larger lancet needles. However, multiple lancing on the same skin location is difficult to accomplish when using a lancing device designed for a single lancing.

Multiple Lancing Device

In implementations, a lancing device enables multiple lancing of a lancet needle into a skin area in response to a single triggering action by a user. The lancing device includes mechanisms for driving a linear reciprocal movement of the lancet needle multiple times along an axis in which the lancet needle extends. The lancing device includes an actuator and a lancet connector for connecting the actuator and the lancet needle. The lancing device further includes a housing, which houses at least some components of the lancing device body including the actuator. The lancing device body further includes a trigger to activate the actuator. Once the actuator is activated, the actuator drives the lancet needle to perform the multiple linear reciprocating motion.

Lancing Device

Figure 2:
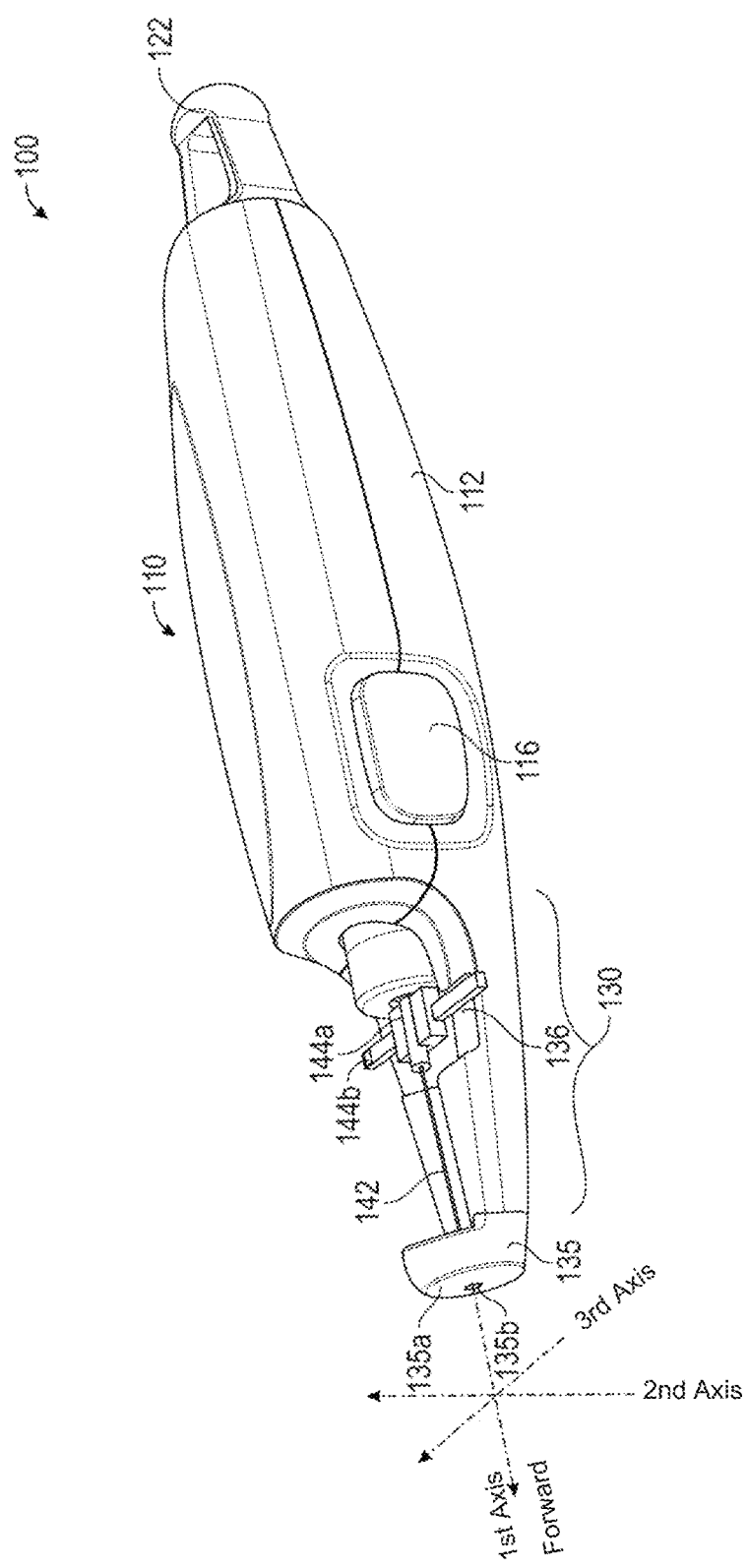
FIG. 2 illustrates the lancing device to which a lancet is coupled according to the implementation of FIG. 1.

FIGS. 1 and 2 illustrate a lancing device 100 for multiple lancing according to an implementation. The lancing device 100 has a lancet 140 and a lancing device body 110 extending along one axis (first axis). In FIG. 1, the lancet 140 and the lancing device body 110 are separate. On the other hand, in FIG. 2, the lancet 140 is engaged with the lancing device body 110. In operation, the lancing device 100 causes a linear reciprocating motion of the lancet 140 multiple times relative to the lancing device body 110, reciprocating between an advanced position and a retracted position in the lancing device body 110 along the first axis.

Lancet

In implementations, the lancet 140 includes a needle or lancet needle 142 and a lancet body 144. A portion of the needle 142 is inserted into the lancet body 144 and fixed to the lancet body 144. The lancet body 144 engages with the lancing device 100 such that the needle 142 extends along the first axis. When the lancet 140 is coupled to the lancing device 100, the needle 142 may not extend to outside the lancing device 100 except when the lancing device 100 is operating for lancing. Accordingly, when the lancing device 100 is not operating to pierce skin, the needle 142 may not come into contact the skin.

Shape of Needle

The needle 142 has an elongated body for piercing the skin. The needle 142 has a generally circular cross-section although not limited thereto. The needle 142 may have a generally tapered shape toward the tip thereof, although not limited thereto. The needle 142 may be in a tubular configuration, although not limited thereto.

Length of Needle

In implementations, the length of the needle 142 beyond the lancet body 144 to its tip is about 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 cm. The length may be in a range between two numbers selected from those listed in the immediately previous sentence. The length of the needle 142 is chosen in view of the size and configuration of the lancing device 100. Also, the length may be chosen in view of the subject to which multiple lancing is used. For example, when the multiple lancing is used for an animal with a thick skin, a longer needle may be appropriate. Again, the needle tip does not extend beyond the lancing device 100 when the device is not operating for lancing.

Diameter of Needle Cross-Section

The diameter of needles is typically represented in a gauge number. For example, a 20 gauge needle has 0.9081 mm outer diameter, a 25 gauge needle has 0.5144 mm outer diameter, a 30 gauge needle has 0.3112 mm outer diameter, and a 34 gauge needle has 0.1842 mm outer diameter. In implementations, the needle 142 for multiple lancing has 36, 35, 34, 33, 32, 31, 30, 29, 28, 27, 26, 25, 24, 23, 22, 21, 20, 19, 18, 17, 16, 15, 14, 13, 12, 11, or 10 gauge number. The gauge number may be in a range between two numbers selected from those listed in the immediately previous sentence. The gauge number of the needle 142 is chosen in view of the skin location and/or the subject to which multiple lancing is applied. A thinner needle is to be used to a skin area of a person where pain receptors are abundant or crowded, and a thicker needle is to be used to a skin area where pain receptors are scarce.

Lancet Body

In an implementation, the lancet body 144 includes a main lancet body 144a. A portion of the needle 142 may be inserted into and supported by the main lancet body 144a. The lancet body 144 is in a size that is larger than the needle 142 and easy for the user to pick up and hold with two fingers. In implementations, the user holds the lancet body 144 and couples it to the lancing device 100.

Lancet Body Wing

In the illustrated implementation, the lancet body 144 additionally includes a lancet body wing 144b. The lancet body wing 144b may extend from the main lancet body 144a in an approximately right angle with the needle 142. The lancet body wing 144b may make it easy for the user to hold the lancet 140.

Lancet Body Engagement Portion

In the illustrated implementation, the lancet body 144 additionally includes a lancet body engagement portion 144c that extends from the main lancet body 144a in the opposite direction to the needle 142. This lancet body engagement portion 144c is configured to engage and couple to the lancing device 100, more specifically to lancet connector 134. When the lancet 140 is properly coupled to the lancet connector 134, the extension of the needle 142 may coincide with the first axis, and the lancet body wing 144b may coincide with the second axis that is perpendicular to the first axis.

Lancing Device Body

In the illustrated implementation of FIG. 1, the lancing device body 110 includes a main body 112, a front-end portion 135, and a lancet receiving portion 130. As illustrated, the lancet receiving portion 130 is interposed between the main body 112 and the front-end portion 135 and connects the two components.

Main Body

In implementations, the main body 112 serves as a housing that accommodates some components of the lancing device 100. The main body 112 may generally extend along the first axis. The main body 112 provides surfaces that a user grips and holds with a hand for use. The main body 112 is in a size and thickness that can be held with one hand.

Front-End Portion

In an implementation, the front-end portion 135 is formed at one end of the lancing device 100. The front-end portion 135 may include a skin contacting surface 135a and a hole 135b formed through the skin contacting surface 135a. The skin contacting surface 135a is to contact with the skin when the lancing device 100 is positioned on the skin for blood sampling. The hole 135b provides a passage through which the needle 142 travels back and forth.

Lancet Receiving Portion

In illustrated implementation, the lancet receiving portion 129 is a portion in which the lancet 140 is accommodated between the front-end portion 135 and the main body 112. The lancet receiving portion 130 includes a lancet guide groove 136a and a recess 136b to receive the lancet body 140 when the lancet 140 is connected to the lancet connector 134. The length of the lancet receiving portion 130 in the first axis may be slightly greater than the overall length of the lancet 140 so that the lancing lancet receiving portion 130 can easily accommodate the lancet 140. In an implementation, the lancet receiving portion 130 may be integrally formed with the main body 112.

Lancet Guide Groove

The lancet receiving portion 130 may include a lancet guide groove 136a that extends along the first axis as shown in FIGS. 1 and 2. The groove 136a may have a shape to accommodate the shape of the lancet main body 144a, and the size of the groove 136 can be slightly greater than the size of the lancet main body 144a. The groove 136 may facilitate aligning the needle 142 when positioning the lancet 140 at the lancet receiving portion 130. In operation, the needle 142 or lancet main body 144a may or may not contact surfaces of the lancet guide groove.

Recess

In implementation, the lancet receiving portion 130 further include a recess 136b that accommodates the lancet body 144 and allows the linear movement of the lancet body 144 along the first axis. In an implementation, at the junction of the guide groove 136a and the recess 136b, a shoulder or step may be defined to restrain movement of the lancet body 144 from advancing more than desired in the forward direction. For example, the step can obstruct and prevent the lancet body 144 from moving further toward the front-end portion 135.

Lancet Connector

The lancet 140 is removably connected to the lancet connector 134 that can couple with the lancet 140 in the lancet receiving portion 130. In an implementation, the lancet connector 134 may include a slot hole 134a to receive the lancet body 144 as shown in FIG. 1. For example, the lancet body engagement portion 144c may be inserted into the slot hole 134a and press-fitted to be secured to the lancet connector 134. The slot hole 134a may be exposed to the outside, which makes it easy to insert the lancet body 144. The lancet connector 134 is disposed adjacent the location where the main body 112 and the lancet receiving portion 130 meet. The lancet connector 134 may include any proper mechanism known in the field to releasably hold the lancet 140. For example, the lancet 140 and the lancet connector 134 may be magnetically connected.

Movement of Lancet Connector

The lancet connector 134 is configured to move along the first axis relative to the main body 112, the lancet receiving portion 130 and the front-end portion 135. Accordingly, the lancet 140 coupled to the lancet connector 134 can also move along the first axis relative to the main body 112, the lancet receiving portion 130 and the front-end portion 135. More specifically, the lancet connector 134 can reciprocate in the forward direction and the backward direction along the first axis relative to the main body 112, the lancet receiving portion 130 and the front-end portion 135.

Actuation Mechanism

The lancing device body 110 further includes an actuation mechanism for driving a linear reciprocating motion of the lancet connector 134. The actuation mechanism is operably connected to the lancet connector 134 and can cause a reciprocating linear motion relative to the lancing device body 110 along the first axis of the lancet connector 134 multiple times with a single activation of the reciprocating actuator.

Reciprocating Actuator

Figure 3:
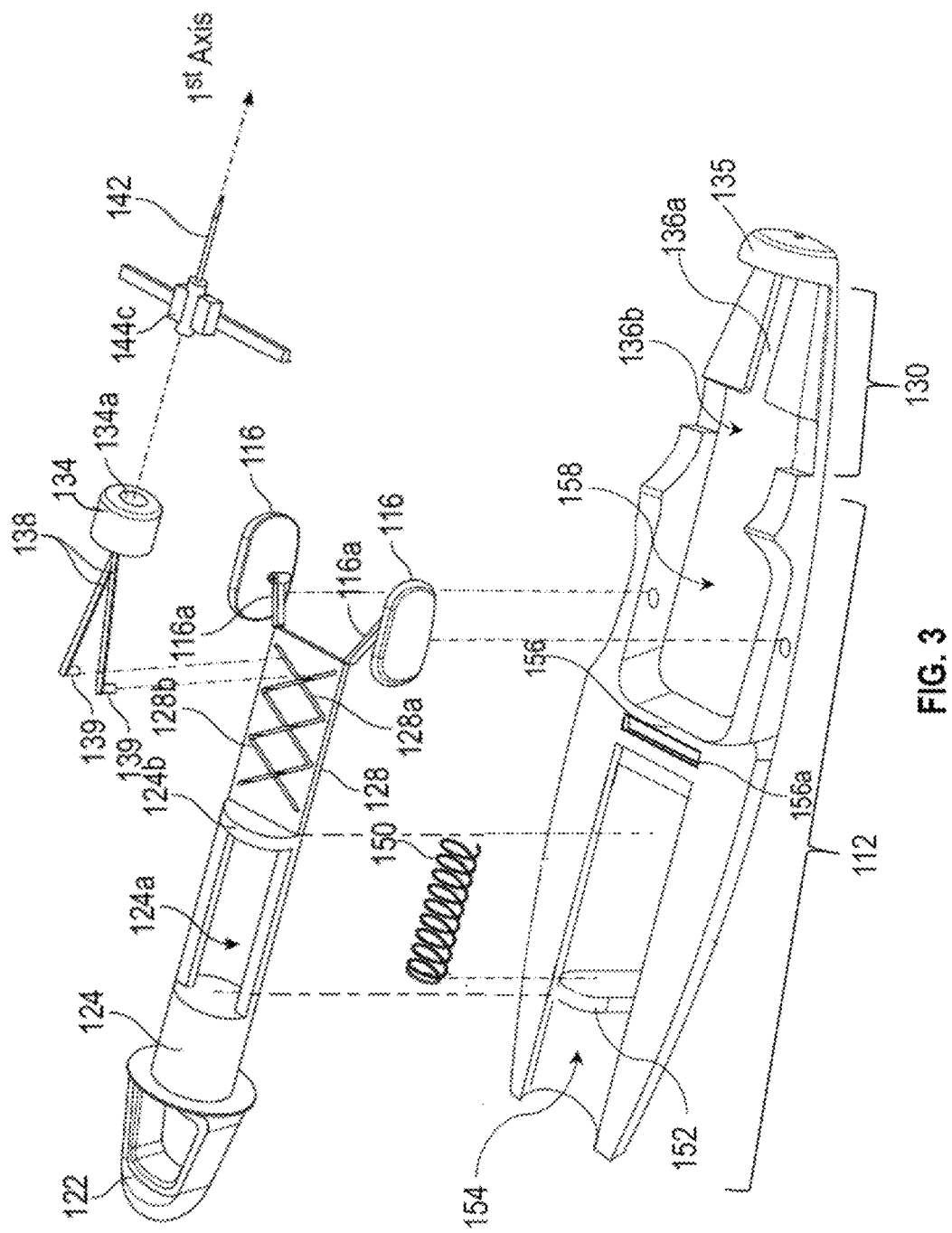
FIG. 3 is an exploded view of the lancing device with its components according to the implementation of FIG. 1.
Figure 4A:
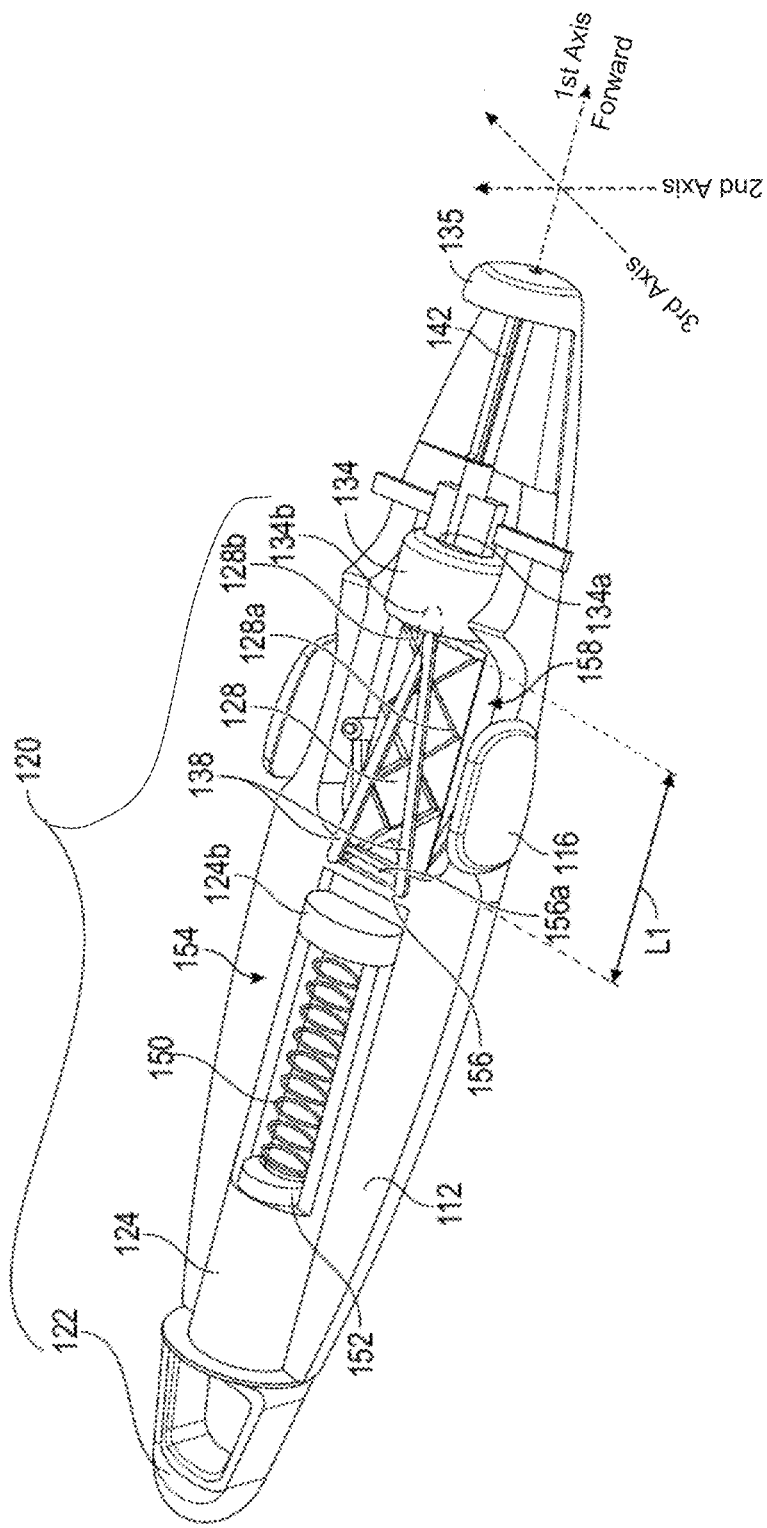
FIG. 4A illustrates components and configuration of the lancing device according to the implementation of FIG. 1 in which the lancing device is in its fully relaxed or released state and the lancet needle does not extend to outside the lancing device.
Figure 4B:
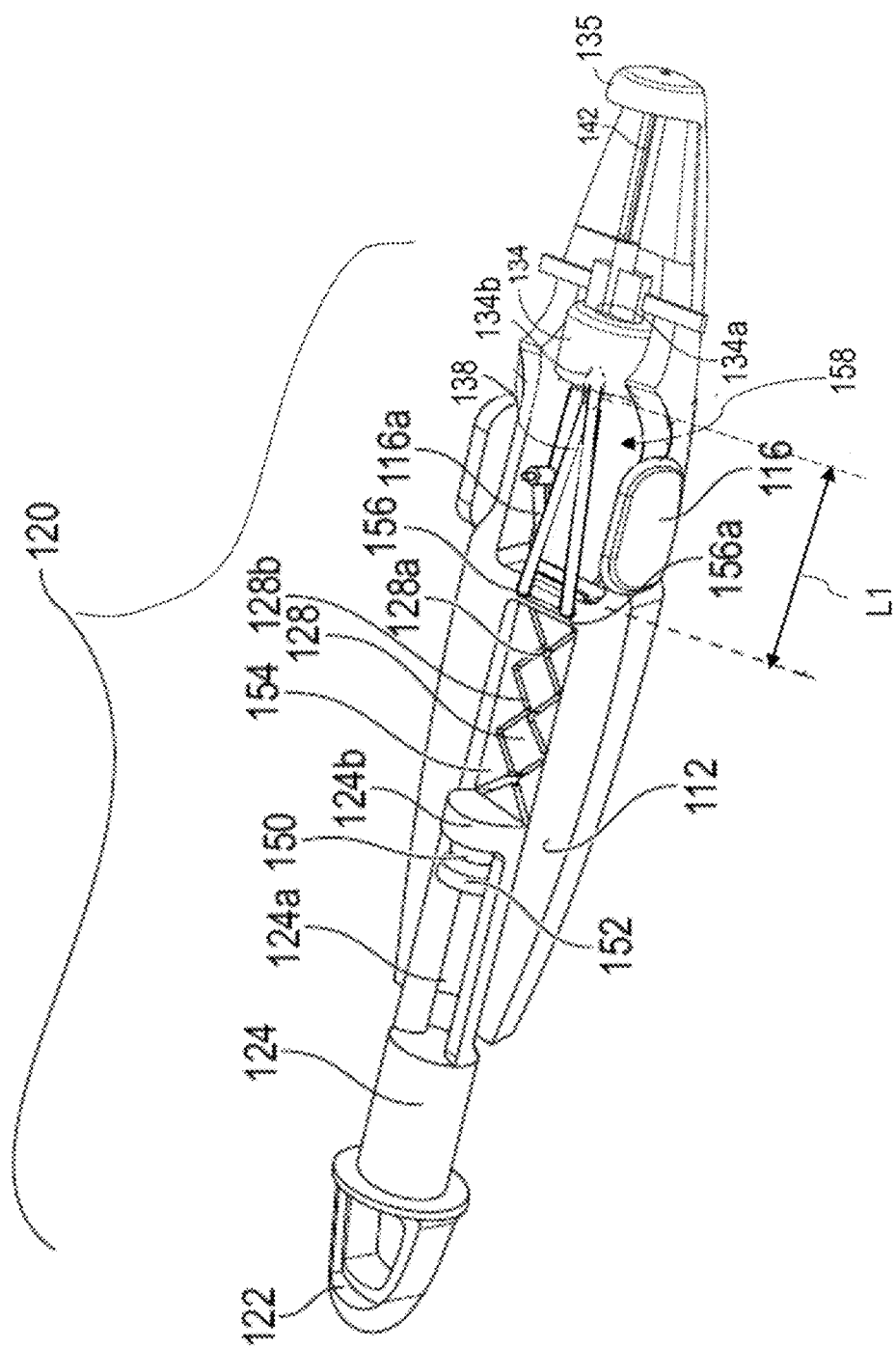
FIG. 4B illustrates interior components and configuration of the lancing device according to the implementation of FIG. 1 in which the lancing device is in its fully loaded state and ready for multiple lancing, and the lancet needle does not extend to outside the lancing device.
Figure 4C:
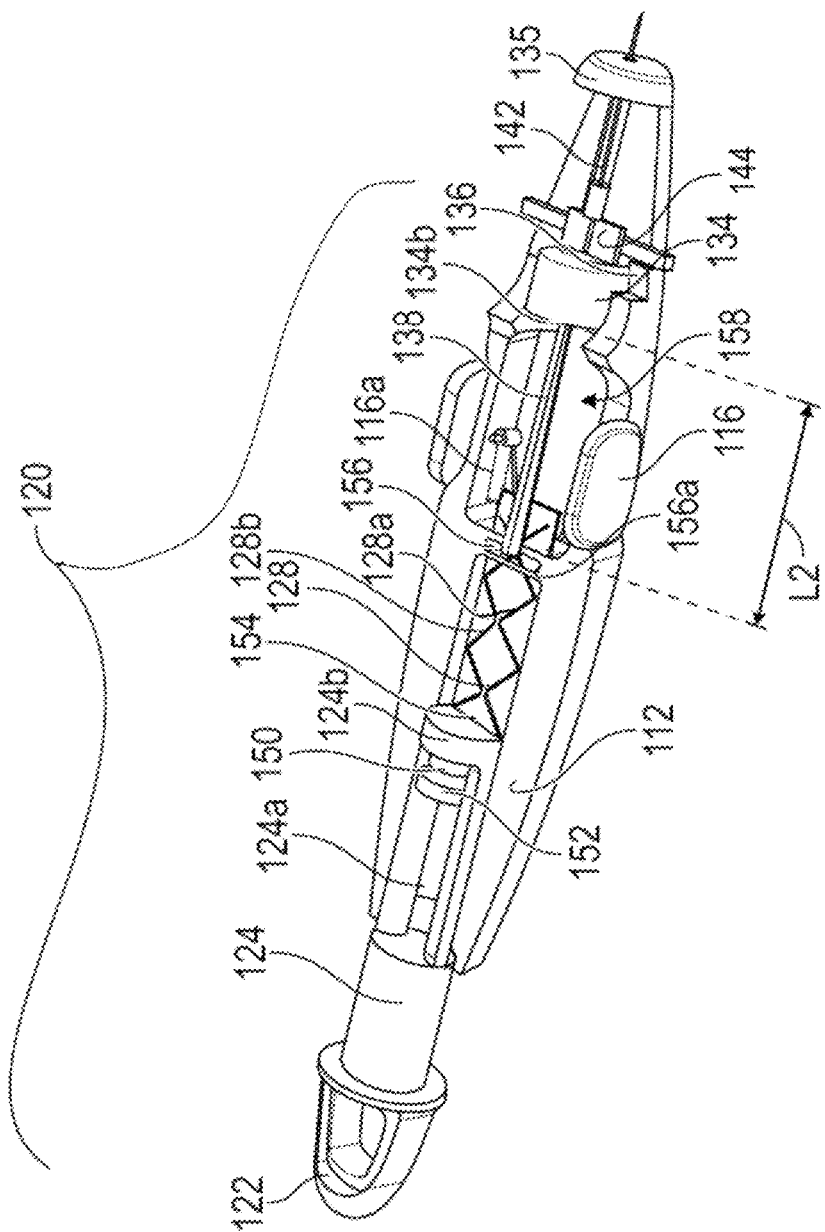
FIG. 4C illustrates interior components and configuration of the lancing device according to the implementation of FIG. 1 in which the lancing device is transitioning from the fully loaded state of FIG. 4B to the fully relaxed state of FIG. 4A and the lancet needle extends to outside the lancing device.

FIGS. 3-4C illustrate a reciprocating actuator 120 disposed in the lancing device body 110 according to one implementation. The illustrated reciprocating actuator 120 includes a handle 122, an actuation member 124, and a guide member 128, a pair of arms 138, a spring 150, and a pair of latches 116a. The reciprocating actuator 120 is operably connected to the lancet connector 134. Upon proper activation to be discussed below, the reciprocating actuator 120 generates a reciprocating linear movement of the lancet connector 134 relative to the lancing device body 110.

Actuation Member

In the illustrated implementation, the actuation member 124 has an elongated body integrated with the handle 122 at one end and the guide member 128 at the other end. The elongated body includes a spring space 124a for accommodating the spring 150 with an end piece 124b. In the illustrated implementation, the handle 122, the actuation member 124 and the guide member 128 are arranged in order and formed in a single piece. For example, the single piece is produced by injection molding to form the single piece component.

Handle

The handle 122 is disposed at one end of the lancing device 100 opposite to the front-end portion along the first axis. The handle 122 is used to pull the handle 122 with one or two fingers of a hand backward in the first axis relative to the main body 112 while gripping the lancing device body 110 with the other hand. The handle 122 is integral to the actuation member 124 such that when pulled backward relative to the main body 112, the actuation member 124 moves together with the handle 122 backward in the first axis relative to the main body 112. The handle 122 may have an opening to insert a finger or two therethrough.

Guide Member

The guide member 128 is a plate integrated with the actuation member 124. The guide member includes two zigzag guide grooves 128a and 128b formed into the plate. Each of the zigzag guide grooves 128a and 128b extends along the longitudinal direction of the elongated body of the actuation member 14 with a repeating zigzag pattern such that the two zigzag guide grooves come close together, move away from each other, and then come close together in the same phase along the first axis. In lieu of the zigzag pattern, the guide grooves 128a and 128b may have a different shape in which two guide grooves are undulating like two sinusoidal curves although not limited thereto.

Main Body Housing Actuator Components

In the illustrated implementation, the main body 112 provides an interior space that houses the actuation member 124, the spring 150, the guide member 128, and the arms 138. The main body 112 may further accommodate at least a portion of the lancet connector 134. Referring to FIGS. 3-4, the main body 112 includes a first accommodating space 154, a second accommodating space 158 and a bridge 156.

First and Second Accommodating Spaces

The first accommodating space 154 may be a groove or channel formed inside the main body 112. The actuation member 124 and the guide member 128 of the actuator 120 are accommodated within the first accommodating space 154 and slidable forward and backward along the first axis relative to the lancing device body 110. The second accommodating space 158 may be a groove or channel formed inside the main body 112.

Bridge

In the illustrated implementation, the first accommodating space 154 and the second accommodating space 158 are separated by the bridge 156. However, the first and second accommodating spaces 154 and 158 are connected with each other via an opening (not shown) underneath the bridge 156.

Guide Member Sliding into Second Accommodation Space

When the actuation member 124 and the guide member 128 are placed in the first accommodating space 154, the guide member 128 may slide into the second accommodating space 158 via the opening underneath the bridge 156. On the other hand, the actuation member 124 may not move into the second accommodating space 158. The bridge 156 blocks movement of the end piece 124b of the actuation member 124 toward the second accommodation space 158.

Spring Stop

A spring stop 152 is formed in the first accommodation space 154 of the main body 112. The spring stop 152 is a wall or partition in the groove or channel of the first accommodation space. When the actuation member 124 is placed in the first accommodation space, the spring stop 152 positions within the spring space 124a and opposes the end piece 124b of the actuation member 124.

Spring

The spring 150 is inserted between the spring stop 152 and the end piece 124b within the spring space 124a of the actuation member 124. The spring 150 may be replaced with an elastic device that can generate power by a linear expansion or compression along its length. One end of the spring 150 abuts and/or is fixed to the end piece 124b of the actuation member 124. The other end of the spring 150 abuts and/or is fixed to the spring stop 152 formed in the first accommodation space 154 of the main body 112. Accordingly, the spring 150 is interposed between one end piece 124b (of the actuation member 124) and the spring stop 152 (of the main body 112). If the spring 150 is a compression spring, the spring accumulates energy in it when the spring is compressed by pushing the handle 122 in the forward direction relative to the lancing device body 112. If the spring is an extension spring, the spring accumulates energy in it when the spring is extended by pulling the handle 122 in the backward direction relative to the lancing device body 112.

When Handle is Pulled from Relaxed State

In case the spring 150 is a compression spring, FIG. 4A illustrates a fully relaxed state of the actuator 120, in which the spring 150 is fully expanded and the guide member 128 is fully advanced into the second accommodation space 158. When the handle 122 is pulled in the backward direction relative to the lancing device body 110 from the relaxed state of FIG. 4A to a loaded state of FIG. 4B, the actuation member 124 and the guide member 128 move backward. A portion of the actuation member 124 extends beyond and outside the lancing device body 110, and the guide member 128 moves from the second accommodation space 158 to the first accommodation space 154. Further, the end piece 124b of the actuation member 124 will compress the spring 150 toward the spring stop 152 of the main body 112, which will load the actuator 120 to the loaded state of FIG. 4B.

Latch to Keep Actuator at Loaded State

A latch 116a may be connected to the actuator 120 inside the main body 112. The latch 116a may selectively keep the actuator 120 at a predetermined position. For example, FIG. 4B illustrates that the latch 116a keeps the actuator 120 at its loaded state, in which the tip of the latch 116a contacts a leading edge of the guide member 128 and blocks the guide member 128 from moving into the second accommodation space 158.

When Latch Releases Actuator

The latch 116a may selectively release the actuator 120 from the predetermined position at the loaded state and start the actuator 120. In implementations, a mechanical or electrical button 116 may cause the latch 116a to release the guide member 128 or the loaded state of the actuator 120.

When the button 116 is pressed from the loaded state of FIG. 4B, the latch 116 may release the guide member 128, which then causes the spring 150 to expand and push the guide member 128 to move into the second accommodation space 158. In an implementation, the button for the latch 116a may be disposed on the side of the main body 112, so that the user can press the button 116 while holding the lancing device 100 with one hand.

Arms

The pair of straight arms 138 operably connects between the guide member 128 and the lancet connector 134 for the linear reciprocal movement of the lancet connector 134. Each arm 138 includes a first connection portion connecting with the lancet connector 134 and a second connection portion connecting with the guide member 128.

First End of Each Arm Connecting with Lancet Connector

Each arm 138 includes the first connection portion at or near its end next to the lancet connector 134. In implementations, the first connection portion (or first end portion) of each arm 138 hingedly connects with a counterpart mechanism provided in the lancet connector 134. For example, the lancet connector 134 includes a hinge pin (not illustrated), and each arm's first connection portion includes a hole that receives the hinge pin, which allows the arm hingedly moves about the hinge pin, i.e., hinge axis of the lancet connector 134 and generally on a plane formed by the first and third axes.

Guide Slit

The bridge 156 separating between the first and second accommodation spaces 154 and 158 extends generally in the third axis. A guide slit 156a is an opening formed through the bridge 156 in the second axis and elongated in the third axis. The guide slit 156a exposes a portion of the guide member 128 passing under the bridge 158 such that a portion of each of the guide grooves 128a and 128b is also exposed through the guide slit 156a.

Second End of Each Arm Connecting with Guide Member via Guide Slit

Each arm 138 includes the second connection portion at or near the other end away from the lancet connector 134. In implementations, the second connection portion (or second end portion) of each arm 138 includes a protrusion 139 that extends generally in the second axis. The protrusion 139 of each arm 138 passes through the guide slit 156a and extends into the space underneath the bridge 156. Further, the protrusion 139 of each arm 138 engages with one of the zigzag guide grooves 128a and 128b exposed immediately below the guide slit 156a.

Movement of Second End of Each Arm

As the guide member 128 slides in the first and second accommodating spaces 154 and 158 along the first axis relative to the main body 112, the protrusion 139 of each arm slides along one zigzag guide groove 128a or 128b of the guide member 128 with which it engages. As the protrusion 139 slides along the zigzag guide groove 128a or 128b, the protrusion 139 also slides along the guide slit 156a because it passes through the guide slit 156a and is guided by the guide slit 156a. Accordingly, each arm's second end portion (from which the protrusion 139 extends) can only move back and forth over the guide slit 156a (from one side to the center of the guide slit) along the third axis. Further, because the two zigzag or undulating guide grooves come close together and move away from each other in the same phase along the first axis, the second end portions of the two arms move synchronously in which they come together toward the center of the guide slit 156a and move away from each other together in the third axis. As the first end portion moves along the third axis, the second end portion of each arm hingedly moves about the hinge axis that passes the lancet connector 134.

Multiple Linear Reciprocation of Lancet Connector

As the two arms 138 move as described above, the lancet connector 134 moves back and forth along the first axis. As the second end portions of the arms 138 move toward the center of the guide slit 156a, the lancet connector 134 advances forward in the first axis. When the second end portions are at the center of the guide slit 156a or at their closest positions in the guide slit, the lancet connector 134 is at the most forward position in the first axis at the distance L2 from the bridge 156 (see FIG. 4C). As the second end portions of the arms 138 move away from the center of the guide slit 156a, the lancet connector 134 retracts backward in the first axis. When the second end portions are at their farthest positions from the center of the guide slit 156a, the lancet connector 134 is at the most backward position in the first axis at the distance L1 from the bridge 156 (see FIGS. 4A and 4B). Since the zigzag or undulating pattern of the guide grooves 128a and 128b repeats multiple times in the guide member 128, the lancet connector 134 moves back and forth multiple times along the first axis.

Multiple Lancing by Single Triggering

The multiple linear reciprocation of the lancet connector 134 is activated by a single triggering action such as pressing the button 116 once. When a lancet 140 is properly coupled with the lancet connector 134, in response to a single triggering, the lancet moves back and forth multiple times along the first axis such that the tip of the lancet needle 142 advances beyond the skin contacting surface 135a and retracts back to behind the skin contacting surface 135a multiple times. If the skin contacting surface 135a is properly placed on a skin surface, in response to a single triggering action, the tip of lancet needle 142 would pierce the skin multiple times and may create multiple openings into the skin surface.

Number of Linear Reciprocation Motion

Upon a single triggering action, the lancet connector 134 performs multiple repetitive linear reciprocating motion, i.e., multiple advancements in the forward direction whether it reaches the most forward position. In the foregoing implementation, the number of zigzag turns of the zigzag guide groove 128a determines the number of multiple advancements. In other implementations discussed below and their variations, the number of advancements would be determined in different manner. In response to a single triggering action, the lancet 140 make the advancements in the forward direction 2, 3, 4, 5, 6, 7, 8, 9, 10, 11, 12, 13, 14, 15, 16, 17, 18, 19 or 20 times upon single triggering activation of the actuator 120. The number of advancements may be in a range formed by two numbers selected from those listed in the previous sentence, for example, 2-6, 3-5, etc.

Time

The multiple linear reciprocating movements completes within about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 seconds from pressing the button or triggering the actuator 120. The time for completing the multiple linear reciprocating movements is in a range formed by two numbers selected from those listed in the previous sentence. For example, the time is between about 0.4 and about 1.5 seconds, between about 0.3 and about 0.9 seconds, etc.

Drawing Blood Using Lancing Device

A user may pierce the skin and take a blood sample using the lancing device 100.

Coupling Lancet to Lancing Device

In an implementation, the user may couple the lancet 140 to the lancing device 100 before using the lancing device. For example, the user holds the lancet body 144 with fingers and moves the lancet 140 generally over the lancet receiving portion 130. Subsequently, the user aligns the lancet needle 142 along the first axis such that the tip of the needle 142 points the forward direction and the lancet body engagement portion 144c faces the lancet connector 134. Then, the user couples the lancet body 144 to the lancet connector 134. For example, the user may insert and press-fit the lancet body engagement portion 144c into the slot hole 134a of the lancet connector 134. Subsequently, the user further aligns the lancet needle 142 with the lancet guide groove 136a such that the tip of the lancet needle 142 would pass the hole 135b of the front-end portion 135. Once the lancet body 144 is properly coupled with the lancet connector 134, the tip of lancet needle 142 would not extend the beyond the skin contact surface 135a.

Loading of the Actuator

Before using the lancing device, the user holds the lancing device body 110 with one hand and pulls the handle 122 with a finger or two of the other hand backward such that the handle 122 moves relative to the lancing device body 110 in the first axis. Pulling the handle 122 away from the lancing device body 110 would turn the actuator 120 from the state of FIG. 4A to its loaded state of FIG. 4B, in which the spring 150 is compressed and the guide member 128 is kept primarily in the first accommodating space 154 by the latch 116a.

Positioning the Lancing Device on the Skin

Once the actuator 120 is in its loaded state, the user positions the lancing device 100 on the skin at a desired location to draw blood. Specifically, the user holds the lancing device 100 with one hand and place it on the desired skin location such that the skin contacting surface 135a of the front-end portion 135 contact the skin of the desired location and further such that the first axis of the lancing device 100 is substantially perpendicular to the plane of the skin surface. After the lancing device 100 is positioned properly, the user presses the skin with the lancing device 100, to tighten contact between the skin contacting space 135a and the skin.

Triggering and Actuation

Subsequently, the user presses the button 116 to trigger the actuator 120, which initiates multiple lancing of the skin. Pressing of the button 116 causes the latch 116a to release and let the guide member 128 move forward to the second accommodation space 158, which would also let the spring 150 expand and push the actuation member 124 in the first axis away from the spring stop 152 of the main body 112. As the spring 150 expands and pushes the actuation member 124, the guide member 128 moves forward further in the first direction and the zigzag guide grooves 128a and 128b of the guide member 128 pass below the guide slit 156a. Then, the second end portion of each arm 138 moves back and forth multiple times in the third axis as the protrusion 139 extending from the second end portion follows the zigzag guide groove 128a or 128b. The multiple movements of the second end portion of each arm 138 in the third axis cause the lancet connector 134 to make multiple linear reciprocating motion in the first axis. Ultimately, the lancet 140 coupled to the lancet connector 134 also makes multiple linear reciprocating motion in the first axis.

Multiple Lancing

Multiple lancing of the skin occurs while the skin contacting surface 135a maintains the contact with the desired location. As the lancet connector 134 advances toward its most advanced position during the multiple linear reciprocating motion, the tip of the lancet needle 142 extends beyond the skin contacting surface 135a in the first axis to pierce the skin of desired location. As the lancet connector 134 retracts backward during the multiple linear reciprocating motion, the lancet needle 142 moves backward in the first axis and is being pulled back from underneath the skin. When the lancet connector 134 is at its most retracted position during the multiple linear reciprocating motion, the lancet needle 142 is retracted such that the tip of the lancet needle 142 does not extend beyond the skin contacting surface 135a and is fully out of the skin. Subsequent to the most retracted position of the lancet connector 134, the lancet connector 134 moves forward to its most advanced position again, which causes the tip of the lancet needle 142 pierces the same skin location where the previous piercing was made or another location that is very adjacent to the previous piercing.

Needle Tip Staying Under Skin

In the alternative, when the lancet connector 134 is at its most retracted position during the multiple linear reciprocating motion, the tip of the lancet needle 142 may still extend beyond the skin contacting surface 135a and stay under the skin. Subsequent to the most retracted position of the lancet connector 134, the lancet connector 134 moves forward to its most advanced position again, which causes the tip of the lancet needle 142 advances more under the skin to further rupture one of the previously ruptured capillaries or one or more adjacent capillaries.

Forming Openings and Rupturing Capillaries

When the lancet 140 launches from the lancing device 100, the tip of the needle 142 pierces and penetrates the skin and ruptures one or more capillaries underneath the skin. When the tip of the needle 142 comes out of the skin as the lancet 140 returns to the lancing device 100, it creates an opening where the needle 142 has penetrated. As the lancet needle 142 pierces and penetrates the skin multiple times, the needle 142 may form one or more openings into the skin. The needle 142 may form multiple openings at slightly different locations as the needle may not pierce the exact same location every time due to slight shaking of the user hand holding the lancing device 100, movement of the actuator 120, etc. In one implementation, the multiple lancing may cause a single large opening.

Collecting Blood

After one or more openings are formed at the skin, the lancing device 100 may be removed. Then, blood will flow out from the openings spontaneously or with some squeezing of areas adjacent to the openings. Then the blood can be collected for analysis, or the blood can be contacted by an analysis device, such as a glucose meter.

Disposal of the Lancet

In an implementation, the lancet 140 may be disposable, and may be disposed after used. For example, after the lancing device 100 is used to form one or more openings, the lancet 140 may be detached from the lancet connector 134 and disposed. For the next blood drawing session, a new lancet 140 may be provided and coupled to the lancet connector.

Additional Actuators

In some implementations, the lancing device 100 may include an actuator mechanism different from the actuator 120 described above. Such an actuation mechanism enables multiple repetitive linear reciprocating motion of the lancet connector upon a single activation of the actuator. In implementations, an actuator includes a reciprocation module configured for generating and/or guiding a linear reciprocation motion and further includes a power module configured for supplying power to actuate the linear reciprocation motion. For examples, the actuator may include a mechanism to translate a certain movement to linear reciprocating motion of the lancet. Some examples of the actuator are discussed below. The lancing device encompassing the actuator described now may be the same as or similar to the lancing device 100, except that the actuator 120 is substituted by another actuator.

Cam Actuator 1

Referring to FIG. 5, an actuator 200 includes a cam shaft 202, a cam 204, and a cam follower 206. The cam 204 is eccentric with respect to the cam shaft 202. The cam follower 206 has a cam follower surface 207 that contacts the circumference (cam surface 205) of the cam 204. As the cam shaft 202 rotates, the cam 204 rotates about the cam shaft 202, the cam follower surface 207 follows the cam surface 205, which causes the cam follower 206 to linearly reciprocate in the distance 210 between an advance (the highest) position and a retracted (the lowest) position. In an implementation, the lancet connector 134 may be coupled to the tip 208 of the cam follower 206. While the cam 204 is in a circular shape, it may be oval or in a different shape.

Cam Actuator 2

Figure 6:
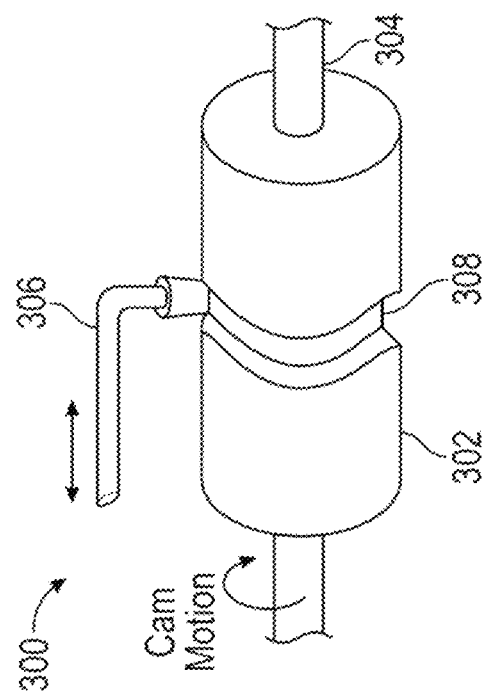
Figure 8:
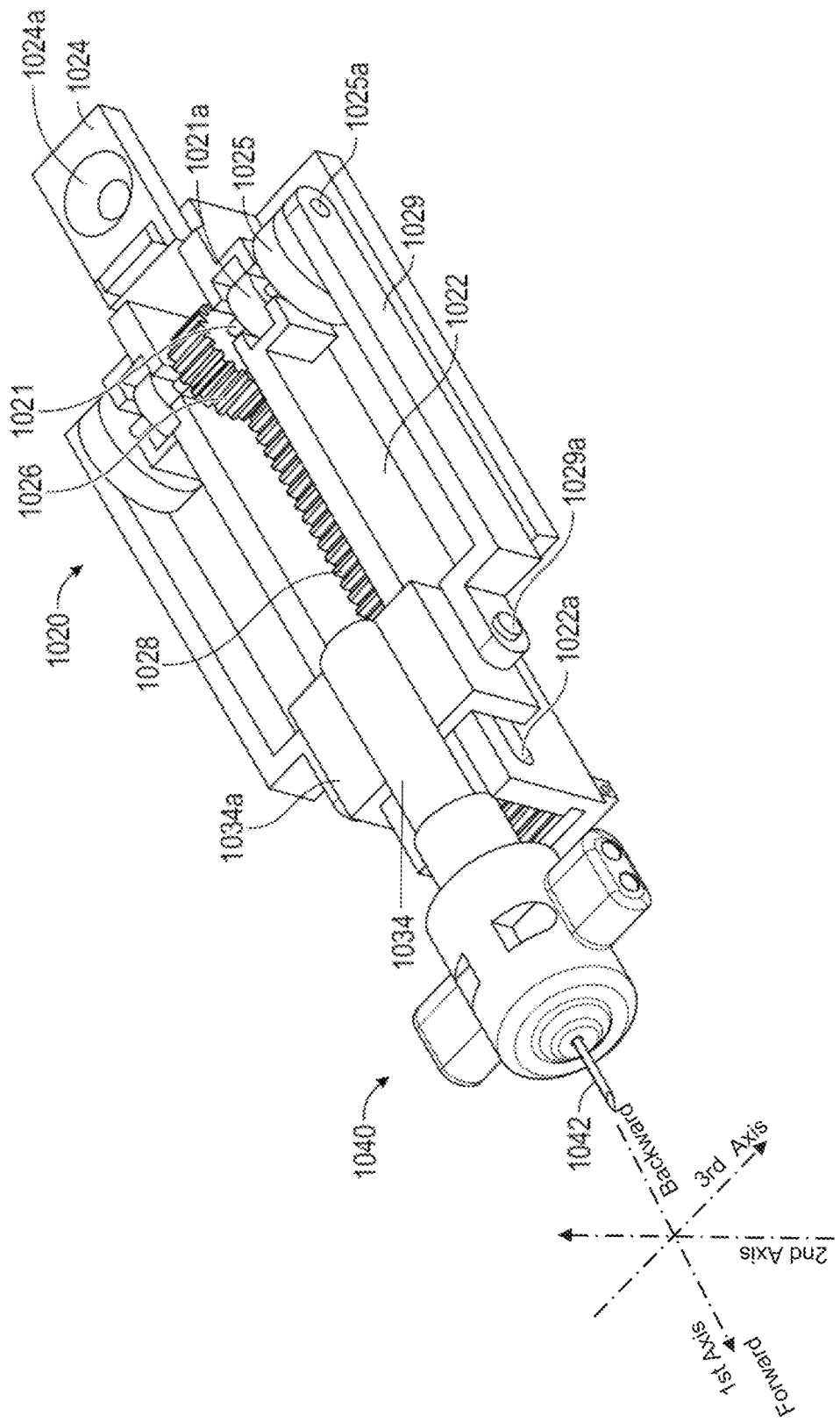
FIG. 8 is a perspective view of an actuator according to an implementation.

Referring to FIG. 6, an actuator 300 may include a cylindrical cam 302, a cam shaft 304, and a cam follower 306. The cam 302 is generally in a cylindrical shape and has a closed-loop groove 308 formed into the circumferential surface of the cylinder. The cam shaft 304 passes the cylindrical cam 302 in alignment with the central axis of the cylinder. One end of the cam follower 306 is inserted in or engages with the groove such that the engaged end of the cam follower 306 follows the closed loop of the groove as the cylindrical cam 302 rotates about the central axis. As the cam shaft 304 rotates, the cylindrical cam 302 rotates about the central axis, the cam follower 306 moves along the closed loop of the groove relative to the cylindrical cam 302, which causes the other end of the cam follower 306 to linearly reciprocate between an advance position and a retracted position along an axis parallel to the central axis. In an implementation, the lancet connector 134 may be coupled to the other end of the cam follower 306.

Cam Actuator 3

Figure 7:
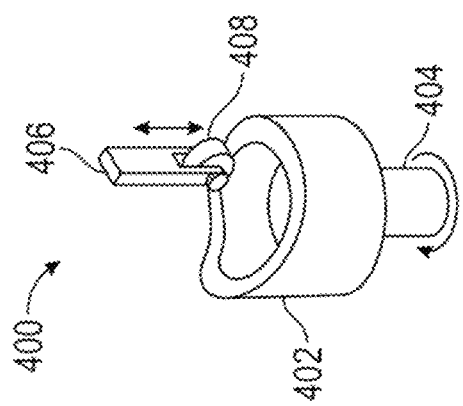

Referring to FIG. 7, an actuator 400 includes a cam 402, a cam shaft 404, and a cam follower 406. The cam 402 has a cylindrical structure that is cut to provide a curved contour 403 on the thickness thereof. The curved contour 403 provides a cam surface of the cam 402. The cam follower 406 has a roller 408 in contact with the curved contour 403 of the cam 402 and follows the curved contour. As the cam shaft 404 rotates, the cam 402 rotates about a central axis of the cylindrical structure, and the roller 408 moves along the curved contour 403 while not actually moving in any direction on a plane perpendicular to the central axis, which causes the cam follower 406 to linearly reciprocate up and down between an advance (the highest) position and a retracted (the lowest) position along an axis parallel to the central axis. In an implementation, the lancet connector 134 may be coupled to the cam follower 406.

Motor Rotating Cam Shaft

In the foregoing cam actuator implementations and their variations, the cam shafts 202, 304, 404 are connected to a motor or a rotational power source for the rotation of the cam shaft. The rotational power source may run with or without an electric motor. In implementations, the button 116 may initiate the motor or another rotational power source to transfer the rotational power to the cam shaft with or without an additional mechanism or electric circuit.

Spring (Mainspring) Rotating Cam Shaft

In some implementations, the cam shaft 202, 304, 404 is connected to a manual rotational mechanism, for example, a mainspring. In one implementation, the lancing device 100 includes a mainspring and by winding the mainspring and releasing the wound mainspring, the cam 204, 302, 402 may rotate by unwinding force of the mainspring.

Actuator 1020

Figure 14:
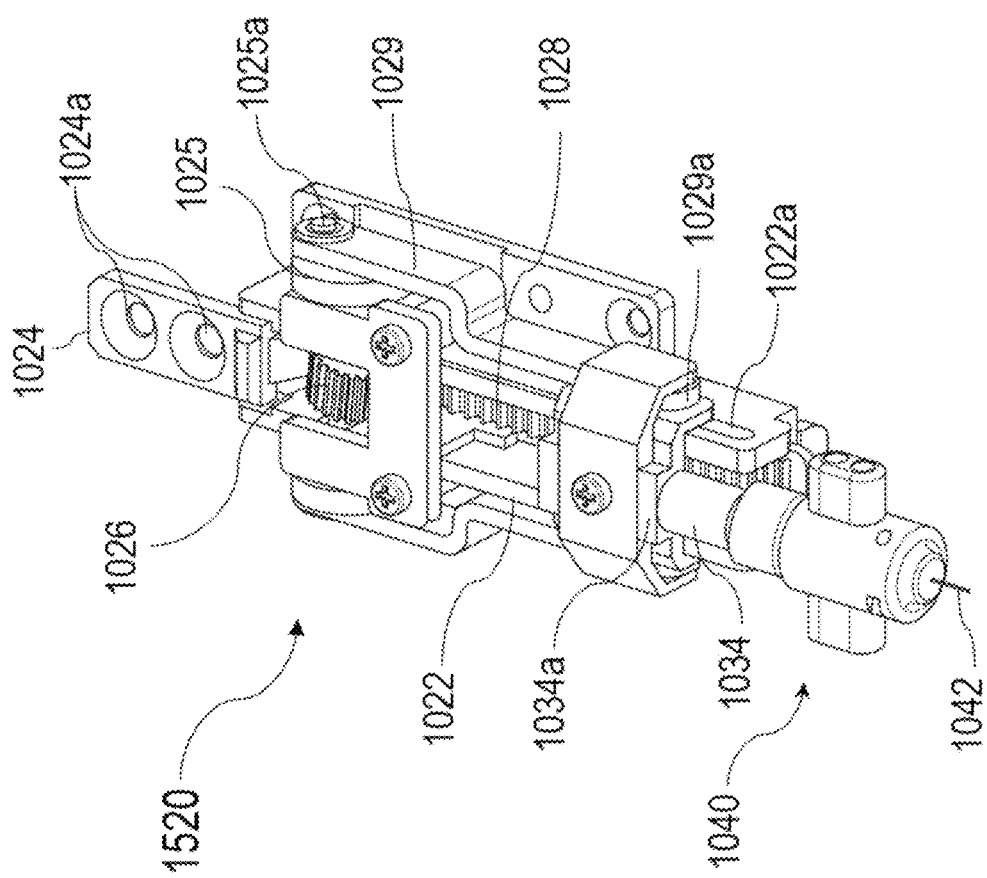
FIG. 14 is a perspective view of another actuator according to an implementation.

FIGS. 8-13 illustrate another actuator 1020 according to an implementation. The actuator 1020 includes an actuator housing 1022, a rack gear 1028, a pinion gear 1026, a cam 1025, and a cam follower 1029 connected to the cam 1025. FIG. 14 is another actuator 1520 that is functionally the same as the actuator 1020 with a slightly different design.

Actuator Housing

The actuator housing 1022 includes two opposing walls that are generally parallel. The actuator housing 1022 accommodates the pinion gear 1026 and the rack gear 1028. Near the front (left in FIGS. 8-14), each wall includes a guide opening 1022a extending along the first axis.

Pinion Gear

The pinion gear 1026 is generally circular and is coupled to a shaft 1021 extending in the third axis such that, when the shaft 1021 rotates, the pinion gear 1026 is to rotate tighter with the shaft 1021. The shaft 1021 is positioned in a fixed location of the actuator housing 1022, and any significant movement except for the rotation may be restricted. The shaft 1021 is restricted from moving along the first, second or third axis relative to the actuator housing 1022 except the rotation and wiggling from the rotation. Accordingly, the pinion gear 1026 is also positioned in a fixed location in the actuator housing 1022, and any movement except for the rotation about the shaft 1021 and associated wiggling is restricted.

Rack Gear

Figure 11:
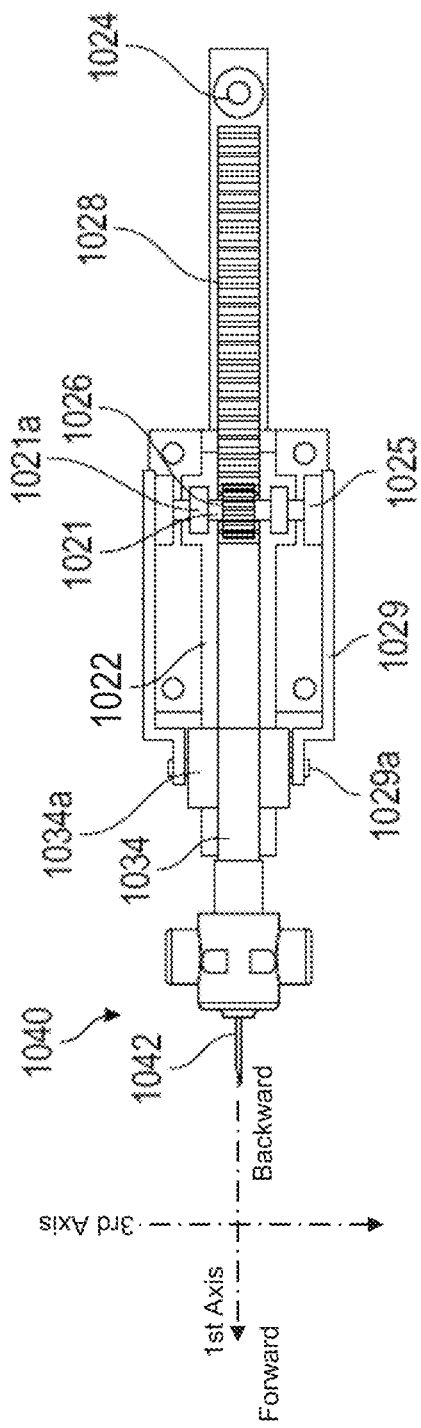
FIG. 11 is a top view of the actuator according to the implementation of FIG. 8 in which the lancing device is in a loaded state.
Figure 12:
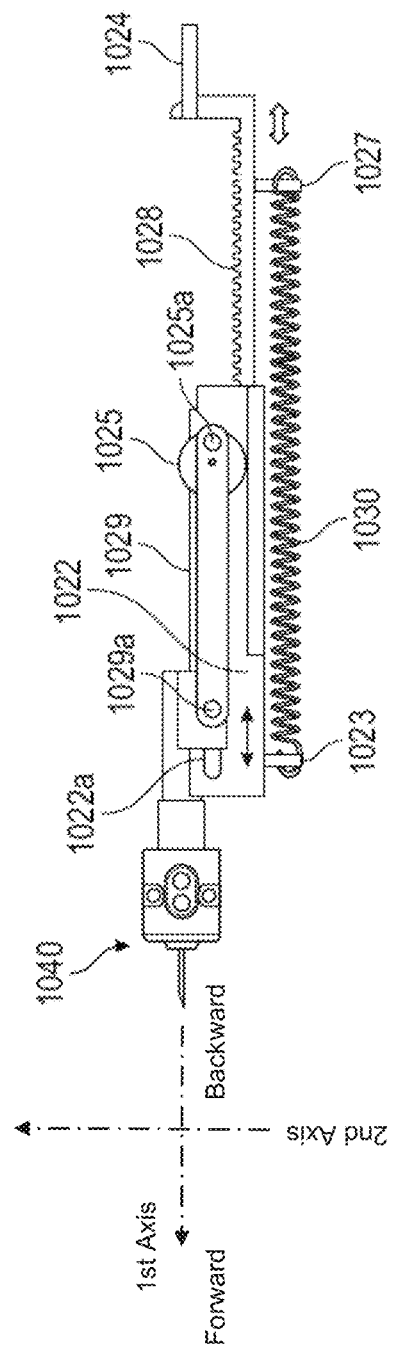
FIG. 12 is a side view of the actuator according to the implementation of FIG. 11.
Figure 13:
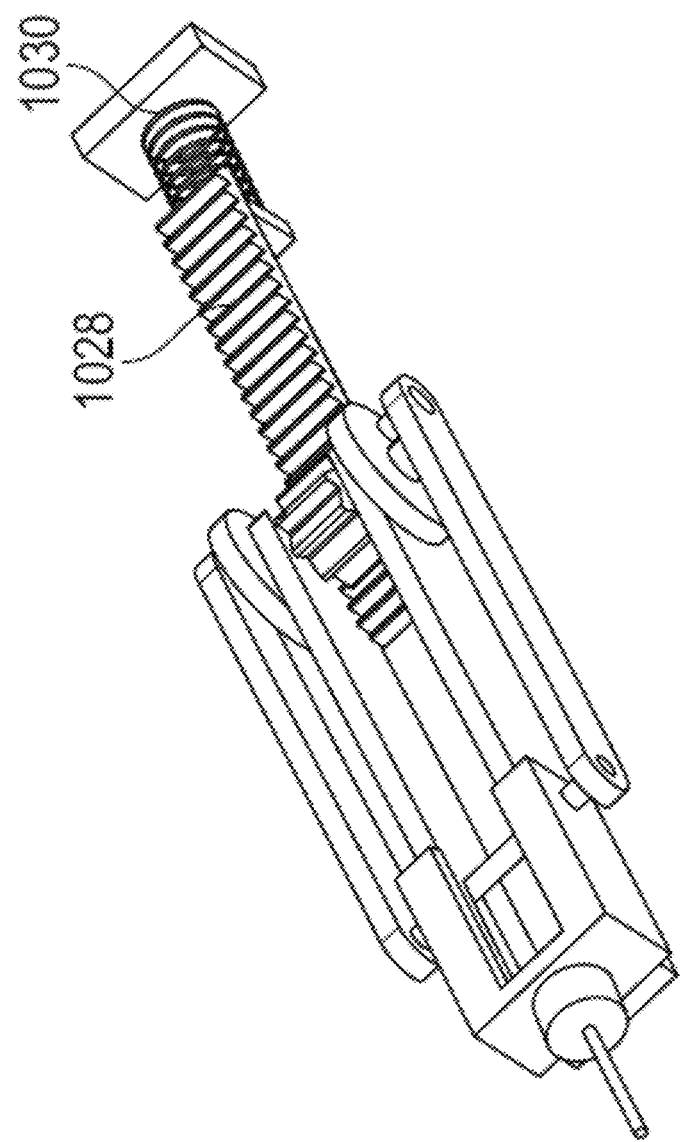
FIG. 13 is a perspective view of another actuator according to an implementation.

The rack gear 1028 is generally linear and extends along or parallel to the first axis. The rack gear 1028 is located between the two opposing walls of the actuator housing 1022 such that the rack gear 1028 can slide forward and backward relative to the actuator housing 1022 along the first axis and may not move in the second axis or the third axis. The actuator housing 1022 may have a rail (not shown) engaged with bottom or side of the rack gear 1028. The rack gear 1028 is configured to slide forward and backward along the first axis relative to the actuator housing 1022 between the forward-most (front) position (FIGS. 9 and 10) and the backward-most (rear) position (FIGS. 11 and 12).

Rack and Pinion Engaged

The pinion gear 1026 is placed on and operably engaged with the rack gear 1028. When the rack gear 1028 slides forward, the pinion gear 1026 rotates about the shaft 1021 clockwise in the view of FIG. 10. When the rack gear 1028 moves backward, the pinion gear 1026 rotates about the shaft 1021 counter-clockwise in the view of FIG. 10.

Gear Ratio

The pinion gear 1026 and the rack gear 1028 have a gear ratio, in which the pinion gear 1026 rotated multiple times when the rack gear 1028 travels along its full length between the front position and the rear position. For example, as the rack gear 1028 travels from the front position to the rear position once, the pinion gear 1026 can rotate 2, 3, 4, 5, 6, 7, 8, 9 or 10 times.

Handle Connector

A handle connector 1024 for connecting to a handle 1222 is integrated to the rack gear 1028. In implementations, the handle connector 1024 is positioned generally at the back end of the rack gear 1028 in the first axis. The handle connector 1024 includes a mechanism, e.g., a through-hole 1024a for coupling with the handle 1222. When the handle 1022 is pulled backward relative to the housing 1010 of the lancing device 1000, the rack gear 1028 slides backward relative to the actuator housing 1022 along the first axis.

Cam

The actuator 1020 includes a pair of cams although not limited thereto. In the illustrated implementation, each cam is connected to one side of the pinion gear 1025 by shaft 1021. Each cam 1025 may be generally circular or oval although not limited thereto. The rotation of the pinion gear 1026 causes rotation of the cam 1025 about the shaft 1021. In the illustrated implementation, the pinion gear 1026 and the cam 1025 have the same rotational axis that passes the shaft 1021. However, the cam 1025 and the pinion gear 1026 may not have the same rotational axis.

Cam Follower

The actuator 1020 includes a pair of cam followers 1029 although not limited thereto. In the illustrated implementation, each cam follower 1029 connects to one of the cam 1025 with its rear end portion. In FIG. 10, the rear end portion of the cam follower 1029 is coupled to a pin 1025a of the cam 1025 at a location other than the rotational axis of the cam 1025. The coupling of the rear end portion of the cam follower 1029 and the pin 1025a of the cam 1025 allows the cam follower 1029 to freely rotate about the pin 1025a. The front end portion of the cam follower 1029 is connected to a lancet connector base 1034a via a pin 1029a that extends in the third axis and passes through both guide openings 1022a formed through the opposing walls of the actuator housing 1022.

Movement of Cam Follower

As the cam rotates about its rotational axis passing the shaft 1021, the pin 1025a rotates around the rotational axis. Then, the rear end portion of the cam follower 1029 connected to the pin 1025a also rotates around the rotational axis, which causes the front end portion of the cam follower 1029 travels forward and backward along the first axis, i.e., linear reciprocation with the forward and backward movement of the pin 1029a in the guide opening 1022a.

Lancet Connector

A lancet connector 1034 has a cylindrical shape with a circular or oval cross-section. In illustrated implementation, the lancet connector 1034 is integral to the lancet connector base 1034a located over the actuator housing 1022, although not limited thereto. The lancet connector base 1034a is integrated to the front end portion of the cam follower 1029 by the pin 1029a. As the front end portion of the cam follower 1029 travels forward and backward in the first axis, the lancet connector base 1034a and the lancet connector 1034 travel forward and backward together with the pin 1029a in the first axis.

Lancet

A lancet 1040 has a lancet body and a lancet needle fixed to the lancet body as discussed in connection with the implementation of FIGS. 1-4C. In implementations, the lancet body includes an engagement portion for engaging with a counterpart portion of the lancet connector 1034. Any mechanical or magnetic engagement is applicable here.

Lancing Device

Figure 15:
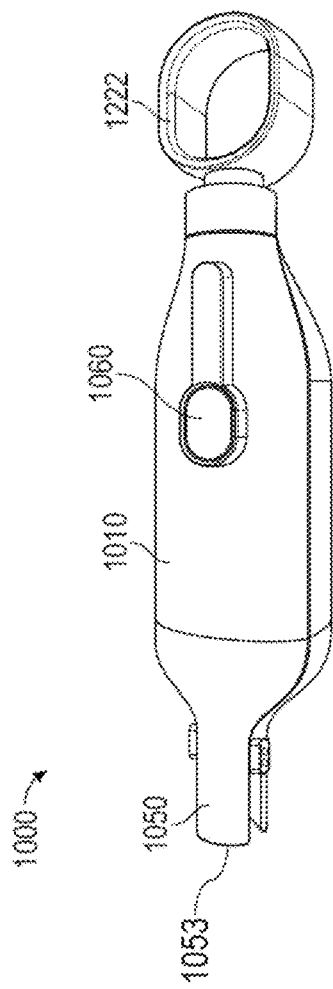
FIG. 15 is a perspective view of a lancing device according to implementations incorporating the actuator of FIG. 8 or FIG. 14, in which the lancing device is fully released.
Figure 16:
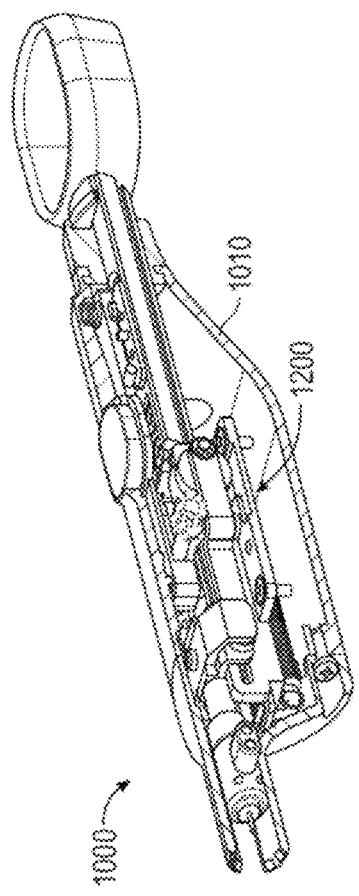
FIG. 16 is a partially cut side view of the lancing device of the implementation of FIG. 15.
Figure 17:
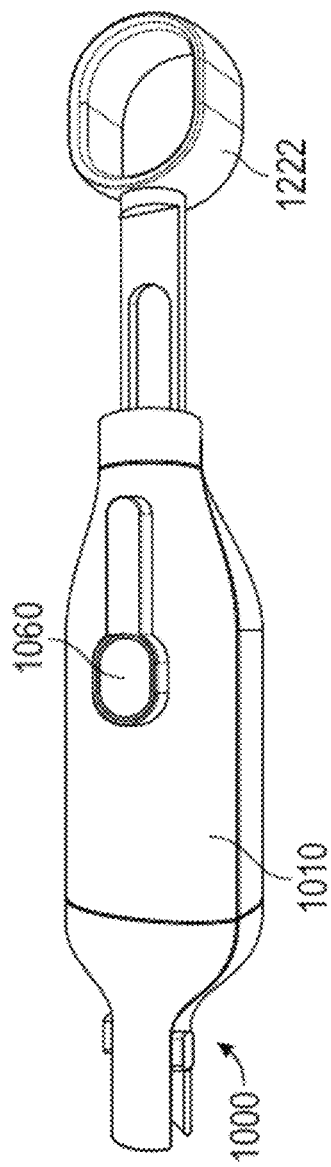
FIG. 17 is a perspective view of the lancing device according to implementations incorporating the actuator of FIG. 8 or FIG. 14, in which the lancing device is fully loaded and ready for multiple lancing.
Figure 18:
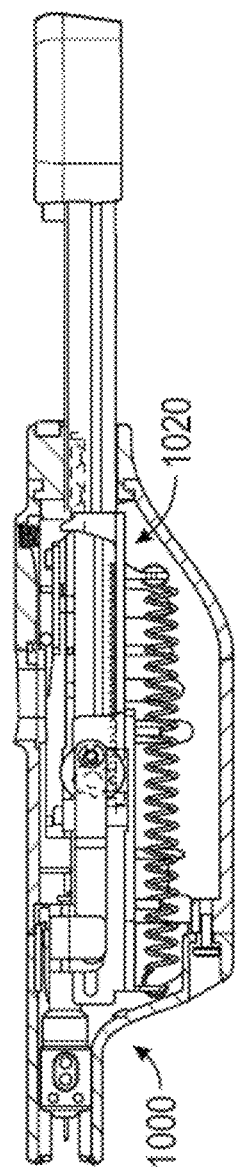
FIG. 18 is a partially cut side view of the lancing device of the implementation of FIG. 17.

FIGS. 15-18 illustrate a lancing device 1000 that incorporates the actuator FIG. 14. The lancing device 1000 includes a front-end portion 1050, a lancing device body 1010, a trigger button 1060 and the handle 1022. FIGS. 15 and 16 illustrate the lancing device 1000 in which the handle 1022 is not pulled away from the lancing device body 1010. FIGS. 17 and 18 illustrate the lancing device 1000 in which the handle 1022 is pulled away from the lancing device body 1010.

Lancet Needle not Exposed

As illustrated in FIGS. 15 and 17, the front-end portion 1050 includes a tip surface or edge that is to contact the skin of desired location for sampling blood. The front-end portion 1050 accommodates the lancet needle 1042 such that the lancet needle 1042 does not extend beyond the front-end portion 1050 in any of the illustrated configurations. However, when the lancing device 1000 is in use for multiple lancing the skin, the lancet needle 1042 is to advance forward in the first axis beyond the tip surface or edge of the front-end portion 1050 and to retract backward multiple times.

Spring

The actuator 1020 includes a spring or elastic member 1030 for providing power for its operation. In implementations, the spring 1030 may extend along the first axis. The spring 1030 may be placed under the rack gear 1028 as in FIGS. 10 and 12. Alternatively, the spring or at least part of it may be placed behind the rack gear 1028 as in FIG. 13. In FIGS. 10 and 12, the front end of the spring 1030 is fixed to a front fixation member 1023 attached to the actuation housing 1022, and the rear end of the spring 1030 is fixed to a rear fixation member 1027 attached to the rack gear 1028.

Extension Spring

When the handle 1222 is pulled backward relative to the main body 1010 from the state of FIGS. 15 and 16 to the state of FIGS. 17 and 18, the rack gear 1028 is also pulled backward relative to the actuator body 1022 from the state of FIGS. 9 and 10 to the state of FIGS. 11 and 12, and the rear fixation member 1027 moves backward and the spring 1030 is extended. If the spring is an extension spring, the extended state of the spring may provide a restorative force to drive the rack gear 1028 back in the forward direction, which would cause the pinion gear 1026 and cam 1025 to rotate and would further cause the linear reciprocation of the pin 1029a and the components integrated thereto.

Compression Spring

When the handle 1222 is pushed forward relative to the main body 1010 from the state of FIGS. 17 and 18 to the state of FIGS. 15 and 16, the rack gear 1028 or handle 1222 is also pushed forward relative to the actuator body 1022 from the state of FIGS. 11 and 12 to the state of FIGS. 9 and 10, the rear fixation member 1027 moves forward and the spring 1030 is compressed. If the spring is a compression spring, the compressed state of the spring may provide a restorative force to drive the rack gear 1028 back in the backward direction, which would cause the pinion gear 1026 and cam 1025 to rotate and would further cause the linear reciprocation of the pin 1029a and the components integrated thereto.

EXAMPLES

Example 1

A multiple lancing device according to the implementation of the lancing device 100 was provided with the 2-times lancing capability by a single trigger action. A lancet with a 30-gauge needle (outer diameter of 0.31 mm) was provided to use with the multiple lancing device. The lancet was installed with the multiple lancing device for the maximum penetration depth to be 1.0 mm.

The multiple lancing device with lancet of Example 1 was positioned at forearm of a human subject and triggered once for blood collection. When blood came out on the skin without squeezing adjacent skin areas, the blood was collected with a MIRAE 3.3G+ glucometer strip available from Osang Healthcare. The overall process of lancing and blood collection was video graphed. Subsequent to blood collection, the subject was asked about the pain level that she/he felt by the lancing with the multiple lancing device in a Numerical Rating Scale (NRS).

Example 2

An "Accu-Chek Softclix" lancing device of Roche was provided. A lancet with a 28-gauge needle (outer diameter of 0.36 mm) was provided to use with the Accu-Chek Softclix lancing device. The lancet was installed with the multiple lancing device for the maximum penetration depth to be 1.0 mm.

The Accu-Chek Softclix lancing device with lancet of Example 6 was positioned at forearm of a human subject and triggered once for blood collection. When blood came out on the skin without squeezing adjacent skin areas, the blood was collected with a MIRAE 3.3G+ glucometer strip available from Osang Healthcare. The overall process of lancing and blood collection was video graphed. Subsequent to blood collection, the subject was asked about the pain level that she/he felt by the lancing with the Accu-Chek Softclix lancing device in a Numerical Rating Scale (NRS).

Example 3

The glucometer strips from Examples 1 and 2 were tested using a Mirae 3.3G glucometer available from Osang Healthcare requiring minimum 0.3 μL to provide a test result.

Example 4

The video recordings of the lancing and blood collection from Examples 1 and 2 were evaluated with the following criteria:

| Score | Evaluation |
| --- | --- |
| 0 | Blood not collected; sampling failure |
| 1 | Blood collected, but insufficient amount for glucometer test; the strip did not get blood |
| 2 | Blood collected, but insufficient amount for glucometer test; the strip was less than half filled with blood |
| 3 | Blood collected, but insufficient amount for glucometer test; the strip was more than half filled with blood, but not enough for glucometer test |
| 4 | Blood collected as much as required for glucometer test |
| 5 | Blood collected more than required for glucometer test |

Example 5

Examples 1 and 2 were performed for total 31 human subjects. The results of Examples 3 and 4 are listed in Table 1.

TABLE 1

| (n = 31) | Accu-Chek Softclix | Multiple Lancing Device |
| --- | --- | --- |
| Skin Penetration Depth | 1.2 mm | 1.0 mm |
| Needle Outside Diameter | 0.36 mm | 0.31 mm |
| Amount of Blood Collected (Scale 0-5) | 1.58 ± 0.81 | 3.87 ± 0.96 |
| Blood glucose measured | 2 out of 31 (6.5%) | 21 out of 31 (68%) |
| Pain Level (Scale 0-10) | 1.39 ± 1.73 | 0.74 ± 1.32 |

As shown in Table 1, the multiple lancing device of Example 1 resulted in less pain to the subjects than Accu-Check Softclix. Further, lancing with the multiple lancing device of Example 1 resulted in more blood collection and a greater chance of success for blood glucose measurement, even if the multiple lancing device of Example 1 had a needle with smaller diameter and shallower penetration depth.

Further Implementations

Scope of the Present Invention

Although the implementations of the inventions have been disclosed in the context of certain implementations and examples, it will be understood by those skilled in the art that the present inventions extend beyond the specifically disclosed implementations to other alternative implementations and/or uses of the inventions and obvious modifications and equivalents thereof. For example, the illustrated implementations of the actuator 120 included a spring as a power source, but it will be understood by those skilled in the art that other power sources known in the art may be used in place of the spring.

Substitution/Combination/Sub-Combination

In addition, while a number of variations of the inventions have been shown and described in detail, other modifications, which are within the scope of the inventions, will be readily apparent to those of skill in the art based upon this disclosure. It is also contemplated that various combinations or sub-combinations of the specific features and aspects of the implementations may be made and still fall within one or more of the inventions. Accordingly, it should be understood that various features and aspects of the disclosed implementations can be combined with or substituted for one another in order to form varying modes of the disclosed inventions. Thus, it is intended that the scope of the present inventions herein disclosed should not be limited by the particular disclosed implementations described above, and that various changes in form and details may be made without departing from the spirit and scope of the present disclosure as set forth in the following claims. For example, a lancing device according to the present invention may include the actuator 1020 and other components described in relation to the lancing device 100. Or a lancing device according to the present invention may include an actuator combining components described herein in relation to different implementation of actuators.

What is claimed is:

1. A lancing device comprising:
    a lancet connector for connecting with a lancet which comprises a lancet body and a needle fixed to and extending from the lancet body;
    a reciprocating actuator operably connected to the lancet connector and configured to cause a linear reciprocating motion of the lancet connector along an axis;

a trigger configured to trigger the reciprocating actuator for causing the linear reciprocating motion of the lancet connector;

a lancing device body comprising a main body portion, a lancet receiving portion and a tip portion that are arranged in order along the axis and integrated to form a single body;

the main body portion being configured for gripping with one hand of a person;

the tip portion comprising a skin contact surface for contacting a skin area from which blood is to be sampled;

the lancet receiving portion interposed between the main body portion and the tip portion therebetween; and a handle disposed outside the lancing device body such that the handle, the main body portion and the lancet receiving portion are arranged in order along the axis, wherein the reciprocating actuator comprises a spring for storing spring energy, wherein the handle operably connected to the reciprocating actuator and is configured for pulling away from the main body portion along the axis, which is to store spring energy in the spring of the reciprocating actuator, wherein the reciprocating actuator comprises a cam configured to rotate about a cam axis and a cam follower operably connected to the cam to move back and forth along the axis, wherein the lancet connector is operably connected to the cam follower for the linear reciprocating motion.

2. The lancing device of claim 1, wherein, upon integrating the lancet with the lancet connector without triggering the reciprocating actuator, the lancet is generally located in or on the lancet receiving portion of the lancing device body, in which the needle extends in a forward direction away from the main body portion along the axis but does not extend beyond the skin contact surface in the forward direction such that a distal end of the needle does not stab the skin area even if the tip portion is place on the skin area, wherein, in response to triggering the reciprocating actuator once with the trigger, the reciprocating actuator is to cause the linear reciprocation motion of the lancet connector along the axis multiple times such that, when the lancet is integrated with the lancet connector, the lancet advances in the forward direction and retreats in a backward direction toward the main body portion along the axis, by which the distal end of the needle travels in the forward direction and in the backward direction multiple times between an advanced position and a withdrawn position, wherein at the advanced position, the distal end of the needle is beyond the skin contact surface in the forward direction such that the needle could pierce the skin area if the skin area contacts the skin contact surface with the axis generally perpendicular to an imaginary plane of the skin area, wherein at the withdrawn position, the distal end of the needle is closer to the main body portion along the axis than at the advanced position such that the needle could not pierce the skin area even if the skin area contacts the skin contact surface with the axis generally perpendicular to the imaginary plane of the skin area.

3. The lancing device of claim 1, wherein the lancet connector comprises an engagement portion configured to connect with a counterpart component of the lancet body for integrating the lancet with the lancet connector, wherein the spring energy is to generate a rotational force to rotate the cam, wherein the trigger is configured to initiate a release of the spring energy.

4. A lancing device comprising:
a lancet connector for connecting with a lancet which comprises a lancet body and a needle fixed to and extending from the lancet body;

a reciprocating actuator operably connected to the lancet connector and configured to cause a linear reciprocating motion of the lancet connector along an axis, wherein the reciprocating actuator comprises a spring for storing spring energy;

a trigger configured to trigger the reciprocating actuator for causing the linear reciprocating motion of the lancet connector;

a lancing device body comprising a main body portion, a lancet receiving portion and a tip portion that are arranged in order along the axis and integrated to form a single body;

the main body portion being configured for gripping with one hand of a person;

the tip portion comprising a skin contact surface for contacting a skin area from which blood is to be sampled;

the lancet receiving portion interposed between the main body portion and the tip portion therebetween; and a handle operably connected to the reciprocating actuator and is configured to move along the axis for storing spring energy in the spring of the reciprocating actuator, wherein the reciprocating actuator comprises a cam configured to rotate about a cam axis and a cam follower operably connected to the cam to move back and forth along the axis, wherein the lancet connector is operably connected to the cam follower for the linear reciprocating motion, wherein the reciprocating actuator further comprises a rack gear elongated generally in the axis and a pinion gear engaged with the rack gear, wherein the pinion gear is operably engaged with the rack gear and further operably connected to the cam such that sliding of the rack gear along the axis causes rotation of the pinion gear which further causes rotation of the cam about the cam axis.

5. The lancing device of claim 4, wherein the handle is connected to the rack gear for sliding the rack gear along the axis relative to the pinion gear when the handle is pulled away from the main body portion along the axis.

6. The lancing device of claim 1, wherein the trigger is located on an exterior of the main body portion such that, when the lancing device body is gripped with one hand of the person, a finger of the same hand or another hand may apply an external force to the trigger, wherein the reciprocating actuator is configured to initiate an actuating operation in response to the external force applied to the trigger.

7. A lancing device comprising:
a lancet connector for connecting with a lancet which comprises a lancet body and a needle fixed to and extending from the lancet body;

a reciprocating actuator operably connected to the lancet connector and configured to cause a linear reciprocating motion of the lancet connector along an axis;

a trigger configured to trigger the reciprocating actuator for causing the linear reciprocating motion of the lancet connector;

a lancing device body comprising a main body portion, a lancet receiving portion and a tip portion that are arranged in order along the axis and integrated to form a single body;

the main body portion being configured for gripping with one hand of a person;

the tip portion comprising a skin contact surface for contacting a skin area from which blood is to be sampled;

the lancet receiving portion interposed between the main body portion and the tip portion there between; and a handle disposed outside the lancing device body such that the handle, the main body portion and the lancet receiving portion are arranged in order along the axis, wherein the reciprocating actuator comprises a spring for storing spring energy, wherein the handle operably connected to the reciprocating actuator and is configured for pulling away from the main body portion along the axis, which is to store spring energy in the spring of the reciprocating actuator, wherein the reciprocating actuator further comprises a zigzag guide member, and an arm operably connected to the zigzag guide member, wherein the axis is referred to as a first axis hereinafter, wherein the zigzag guide member is configured to slide in a forward direction and in a backward direction along the first axis, wherein the forward direction is from the main body portion to the tip portion along the first axis, and the backward direction is from the tip portion to the main body portion along the first axis, wherein the zigzag guide member is operably connected to the spring such that, when the zigzag guide member moves in the backward direction, the spring is to be compressed and store spring energy, and further such that, as the spring energy is released, the spring is to extend and move the zigzag guide member in the forward direction, wherein the zigzag guide member comprises a zigzag guide, wherein the arm comprises a first connection portion hingedly connected with the lancet connector for hinged rotation relative to the lancet connector about a second axis generally perpendicular to the first axis, wherein the arm comprises a second connection portion distanced from the first connection portion and engaged with the zigzag guide such that the second connection portion is to travel along the zigzag guide as the zigzag guide member moves in the forward direction and in the backward direction along the first axis, wherein the arm further comprises a third connection portion distanced from the first connection portion and engaged with a linear guide that is provided inside the main body portion and extends in a third axis generally perpendicular to the first axis and further to the second axis such that the third connection portion is to travel along the linear guide between two lateral positions in the third axis, wherein the trigger is configured to initiate a release of the spring energy, wherein when the spring energy is released, the zigzag guide member slides in the forward direction, which causes the second connection portion to travel relative to the zigzag guide member along the zigzag guide, which further causes the hinged rotation of the arm about the second axis relative to the lancet connector, while the third connection portion of the arm travels along the linear guide between the two lateral positions in the third axis, which further causes the arm to push the lancet connector in the forward direction and pull the lancet connector in the backward direction to make the linear reciprocating motion of the lancet connector.

8. The lancing device of claim 7, wherein the zigzag guide comprises at least one guide groove formed into the zigzag guide member that extends in a zigzag pattern when viewed in the second axis, wherein the second connection portion of the arm is sized and shaped for engaging with the at least one guide groove for traveling along the third axis as the zigzag guide member slides in the forward direction and in the backward direction.

9. The lancing device of claim 7, wherein the zigzag guide comprises at least one guide rail formed on the zigzag guide member that extends in a zigzag pattern when viewed in the second axis, wherein the second connection portion of the arm is sized and shaped for engaging with the at least one guide rail for traveling along the third axis as the zigzag guide member slides in the forward direction and in the backward direction.

10. The lancing device of claim 7, wherein the linear guide comprises a linear guide channel defined inside the main body portion and extending in the third axis, wherein the third connection portion is inserted in the linear guide channel and restricted to travel only along the linear guide channel between the two lateral positions in the third axis.

11. The lancing device of claim 7, wherein the arm is configured to hingedly rotate on an imaginary plane generally parallel to a plane defined by the first axis and the third axis, wherein the second connection portion extends generally in the second axis further from the third connection portion to engage with the zigzag guide.

12. The lancing device of claim 7, wherein the reciprocating actuator further comprises a spring guide configured to guide and keep the spring within a space it defines as the spring compresses and extends, wherein the spring guide comprises a spring contact surface which one end of the spring contacts.

13. The lancing device of claim 12, wherein the zigzag guide member is integrated with the spring guide, wherein, as the spring energy is released, the spring is configured to push the spring contact surface, which causes the spring guide to travel in the forward direction and accordingly moves the zigzag guide member in the forward direction relative to the main body portion.

14. The lancing device of claim 12, wherein the handle is connected to the spring guide and configured to be pulled in the backward direction relative to the main body portion, which causes the spring guide to travel in the backward direction and compresses the spring, wherein the reciprocating actuator further comprises a latch configured to stop the handle from being pulled in the backward direction beyond a predetermine point in the main body portion, at which the spring is compressed and stores the spring energy, wherein the trigger is configured to initiate the release of the spring energy.

15. The lancing device of claim 1, wherein the lancet receiving portion comprises a channel extending in the axis for aligning the needle when connecting the lancet to the lancet connector.

16. The lancing device of claim 15, wherein the lancet receiving portion further comprises a recess configured to receive the lancet body and to permit a linear movement of the lancet body along the axis.

17. The lancing device of claim 15, wherein the lancet receiving portion further comprises a step configured to block the lancet body from advancing in a forward direction beyond the tip portion.

18. The lancing device of claim 1, wherein the lancet comprises at least one wing extending from the lancet body in a direction generally perpendicular to the extension of the needle from the lancet body.

19. A lancing system comprising:
a lancet connector for connecting with a lancet which comprises a lancet body and a needle fixed to and extending from the lancet body;
a reciprocating actuator operably connected to the lancet connector and configured to cause a linear reciprocating motion of the lancet connector along an axis;
a trigger configured to trigger the reciprocating actuator for causing the linear reciprocating motion of the lancet connector;
a lancing device body comprising a main body portion, a lancet receiving portion and a tip portion that are arranged in order along the axis and integrated to form a single body;
the main body portion being configured for gripping with one hand of a person;
the tip portion comprising a skin contact surface for contacting a skin area from which blood is to be sampled, the tip portion further comprising an opening through which the needle is to travel; and
the lancet receiving portion interposed between the main body portion and the tip portion there between,
wherein the lancet connector comprises an engagement portion configured to connect with a counterpart component of the lancet body for integrating the lancet with the lancet connector,
wherein, upon integrating the lancet with the lancet connector without triggering the reciprocating actuator, the lancet is generally located in or on the lancet receiving portion of the lancing device body, in which the needle extends in a forward direction away from the main body portion along the axis but does not extend beyond the skin contact surface in the forward direction such that a distal end of the needle does not stab the skin area even if the tip portion is place on the skin area,
wherein, in response to triggering the reciprocating actuator once with the trigger, the reciprocating actuator is to cause the linear reciprocation motion of the lancet connector along the axis multiple times such that, when the lancet is integrated with the lancet connector, the lancet advances in the forward direction and retreats in a backward direction toward the main body portion along the axis, by which the distal end of the needle travels in the forward direction and in the backward direction multiple times through the opening between an advanced position and a withdrawn position, wherein at the advanced position, the distal end of the needle is beyond the skin contact surface in the forward direction such that the needle could pierce the skin area if the skin area contacts the skin contact surface with the axis generally perpendicular to an imaginary plane of the skin area, wherein at the withdrawn position, the distal end of the needle is closer to the main body portion along the axis than at the advanced position such that the needle could not pierce the skin area even if the skin area contacts the skin contact surface with the axis generally perpendicular to the imaginary plane of the skin area, wherein the reciprocating actuator comprises a cam configured to rotate about a cam axis and a cam follower operably connected to the cam to move in the forward direction and the backward direction along the axis, wherein the lancet connector is operably connected to the cam follower for the linear reciprocating motion, wherein the reciprocating actuator further comprises a rack gear elongated generally in the axis and a pinion gear engaged with the rack gear, wherein the pinion gear is operably engaged with the rack gear and further operably connected to the cam such that sliding of the rack gear along the axis causes rotation of the pinion gear which further causes rotation of the cam about the cam axis, wherein the reciprocating actuator further comprises a handle disposed outside the main body portion and configured for pulling in the backward direction along the axis relative to the lancing device body, wherein the handle is connected to the rack gear for sliding the rack gear in the backward direction relative to the pinion gear when the handle is pulled in the backward direction.

\* \* \* \* \*